(12) United States Patent
Reisman

(10) Patent No.: US 7,604,939 B2
(45) Date of Patent: Oct. 20, 2009

(54) METHODS OF IDENTIFYING ACTIVE BRM EXPRESSION-PROMOTING HDAC INHIBITORS

(75) Inventor: David Reisman, Dexter, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 11/365,268

(22) Filed: Mar. 1, 2006

(65) Prior Publication Data
US 2006/0292594 A1 Dec. 28, 2006

Related U.S. Application Data

(60) Provisional application No. 60/657,603, filed on Mar. 1, 2005.

(51) Int. Cl.
C12Q 1/68 (2006.01)
(52) U.S. Cl. .......................................... 435/6; 435/7.1
(58) Field of Classification Search ....................... None
See application file for complete search history.

(56) References Cited

U.S. PATENT DOCUMENTS

| | | | |
|---|---|---|---|
| 5,055,608 A | 10/1991 | Marks et al. | |
| 5,175,191 A | 12/1992 | Marks et al. | |
| 5,369,108 A | 11/1994 | Breslow et al. | |
| 5,700,811 A | 12/1997 | Breslow et al. | |
| 5,773,474 A | 6/1998 | Breslow et al. | |
| 5,922,837 A | 7/1999 | Meinke et al. | |
| 5,993,845 A | 11/1999 | Geerts et al. | |
| 6,541,661 B1 | 4/2003 | Delorme et al. | |
| 6,638,530 B1 | 10/2003 | Ishibashi et al. | |
| 6,706,686 B2 | 3/2004 | Long et al. | |
| 6,784,173 B2 | 8/2004 | Leser-Reiff et al. | |
| 6,825,317 B2 | 11/2004 | Nishino et al. | |
| 2002/0103192 A1 | 8/2002 | Curtin et al. | |
| 2002/0177594 A1 | 11/2002 | Curtin et al. | |
| 2003/0013757 A1 | 1/2003 | Leser-Reiff et al. | |
| 2003/0129724 A1 | 7/2003 | Grozinger et al. | |
| 2003/0206946 A1 | 11/2003 | Chung | |
| 2004/0077698 A1 | 4/2004 | Georges et al. | |
| 2004/0132825 A1 | 7/2004 | Bacopoulos et al. | |
| 2004/0214860 A1 | 10/2004 | Charous et al. | |
| 2004/0224991 A1 | 11/2004 | Lu et al. | |
| 2004/0229889 A1 | 11/2004 | Urano et al. | |
| 2005/0032831 A1 | 2/2005 | Kozikowski et al. | |

FOREIGN PATENT DOCUMENTS

| EP | 1426054 | 8/2002 |
|---|---|---|
| WO | WO 01/18171 | 3/2001 |
| WO | WO0215921 | 2/2002 |
| WO | WO2004046094 | 6/2004 |
| WO | WO2004113336 | 12/2004 |

OTHER PUBLICATIONS

Yamamichi-Nishina et al. (JBC, vol. 278(9), pp. 7422-7430, Feb. 2003.*
Wang et al., "he SWI/SNF family of ATP-dependent chromatin remodelers: similar mechanisms for diverse functions," Curr. Top. Microbiol. Immunol., 2003, 274:143-69.
Reisman et al., "Concomitant down-regulation of BRM and BRG1 in human tumor cell lines: differential effects on RB-mediated growth arrest vs CD44 expression.," Oncogene, 2002, 21(8):1196-207.
Reisman et al., "Loss of BRG1/BRM in human lung cancer cell lines and primary lung cancers: correlation with poor prognosis," Cancer Res., 2003, 63(3), 560-6.
Yoshida et al., "Trichostatin A and trapoxin: novel chemical probes for the role of histone acetylation in chromatin structure and function," Bioassays 17, 423-430 (1995).
Saito et al., "A synthetic inhibitor of histone deacetylase, MS-27-275, with marked in vivo antitumor activity against human tumors," PNAS USA 96, 4592-4597, (1999).
Furamai et al., "Potent histone deacetylase inhibitors built from trichostatin A and cyclic tetrapeptide antibiotics including trapoxin.," PNAS USA 98 (1), 87-92 (2001).
Komatsu et al., "Cyclic hydroxamic-acid-containing peptide 31, a potent synthetic histone deacetylase inhibitor with antitumor activity.," Cancer Res. 61(11), 4459-4466 (2001).
Lee et al., "MS-275, a histone deacetylase inhibitor, selectively induces transforming growth factor beta type II receptor expression in human breast cancer cells," Cancer Res. 61(3), 931-934 (2201).
Suzuki et al., "Synthesis and histone deacetylase inhibitory activity of new benzamide derivatives," J. Med. Chem. 42(15), 3001-3003 (1999).
Bourachot et al., "Growth inhibition by the mammalian SWI-SNF subunit Brm is regulated by acetylation," EMBO (2003) 24 pg. 6505-6515.
Qian et al., "argeting tumor angiogenesis with histone deacetylase inhibitors: the hydroxamic acid derivative LBH589," Clin. Cancer. Res., 2006, 12(2):634-42.
Remiszewski et al., "N-hydroxy-3-phenyl-2-propenamides as novel inhibitors of human histone deacetylase with in vivo antitumor activity: discovery of (2E)-N-hydroxy-3[4-[[(2-hydroxyethyl)[2-(1H-Indol-3-yl)ethyl]amino] methyl]phenyl]-2-propenamide (NVP-LAQ824).," J. Med. Chem., 2003, 46(21):4609-24.

(Continued)

Primary Examiner—Larry R. Helms
Assistant Examiner—Meera Natarajan
(74) Attorney, Agent, or Firm—Casimir Jones SC

(57) ABSTRACT

The present invention provides screening methods for identifying BRM expression-promoting histone deacetylase (HDAC) inhibitors, diagnostic methods for determining the suitability of treatment of a candidate subject with a BRM expression-promoting HDAC inhibitor, and therapeutic methods for treating cancer cells in a patient with a BRM expression-promoting HDAC inhibitor. The present invention also provides BRG1 and BRM diagnostics, methods for increasing a cancer patient's resistance to viral infection, and methods for determining the suitability of treatment of a candidate subject with a glucocorticoid compound or retinoid compound.

15 Claims, 5 Drawing Sheets

OTHER PUBLICATIONS

Schroeder and Neagle, "FLIPR: A New Instrument for Accurate, High Trhoughput Optical Screening," J. Biomol. Screening 1:75 [1996].

Glaser et al., "Role of class I and class II histone deacetylases in carcinoma cells using siRNA.," Biochemical and Biophysical Res. Comm., 310:529-36, 2003.

Wong et al., "BRG1, a component of the SWI-SNF complex, is mutated in multiple human tumor cell lines.," Cancer Res. 60:6171-6177, 2000.

Miller et al., "Induction of a high incidence of lung tumors in C57BL/6 mice with multiple ethyl carbamate injections," Cancer Lett, 198:139-144, 2003.

Yamamichi et al., "The Brm gene suppressed at the post-transcriptional level in various human cell lines is inducible by transient HDAC inhibitor treatment, which exhibits antioncogenic potentia," Oncogene (2005) 1-11.

Su et al. "A Novel Histone Deacetylase Inhibitor Identified by High-Throughput Transcriptional Screening of a Compound Library," Cancer Res 60 (12): 3137 (2000).

Bourachot et al. Growth inhibition by the mammalian SWI-SNF subunit Brm is regulated by acetylation. The EMBO Journal. 2003. vol. 22, No. 24; p. 6505-6515.

Yamamichi-Nishina et al. SW13 cells can transition between two distinct subtypes by switching expression of BFG1 and Brm genes at the post-transcription level. J of Biological Chemistry. Feb. 2003. vol. 278, No. 9; p. 7422-7430.

Mizutani et al. Maintenance of integrated proviral gene expression requires Brm, a catalytic subunit of SWI/SNF complex. J of Biological Chemistry. May 2002. vol. 277, No. 18; p. 15859-15864.

Wong et al. BRG1, a component of the SWI-SNF complex, is mutated in multiple human tumor cell lines. Cancer Research. Nov. 2000. vol. 60; p. 6171-6177.

Reisman et al. Concomitant down-regulation of BRM and BRG1 in human tumor cell lines; differential effects on RB-mediated growth arrest vs. CD44 expression. Oncogene. 2002. vol. 21; p. 1196-1207.

* cited by examiner

Human BRM Promoter (SEQ ID NO:42) with a 7-BP Insertion Starting at Position 741 Underlined

```
TTAGCGAAGATGGCAGGTGAGGGAAGGTTATAGTGCTGTACCTAGTCCACGAAGTAAACAGAGAGGTTAGG
GTGGGTTTACTTATTTATAAGGCGTTCAGCCTCTCAGCTGTTTCTCCCTCGTTGGCATTTGGAAGCTTGCA
GTCCTTCAGGGAAGAGACAGATTTGGCAGGAACGTTCTTTGTGCCCGCCTCCCTTTTCtattttTATTTT
TTATTTTTTTACCTGGAATAGGGGGCAGATTTATAATGACAGCCTTAGGGAAGGGGGAGAAAAAGTTTCAG
CCGGCACGACAATGCCCGTTTTTTCCACAGTCCACACTGTGCCACAAACAGCTTTGGTGCCACTCGGAGCC
CGTCCCCCGTCCCCTCCCTCTCTCTGCAGGCTCGCACTGGCAGGCGGAGGCACAGTTAAATTCCAGCAC
CTTCTCCACATACCCCCGAACTACTACGCGCTATTACTACGGCTGCCCTCCGTTTTCGCTTCGCCTCCTCC
CCTTCCGCAGTCTCCCTGGAGGAGCCCCGCGGCGCCCGAGGAAGAGGACTGCCAGGGAAGGGACAGCGGGC
GCCCAGCTCCAGCAGGGCTTGGGGCTTTCTGCATCCCGCGCAGTTTCTCTGCTCCAGGCACAAACGCGGCC
CGAGAGCCGGCGCCTTGCAGTCACACACGGATCCACGCATACAGTAGAGCTGTCTAGATCCACATTCTTGC
ACACCGCCCCCTCCTCCCCCCGCGCTCCCGGAGTCGCTGAGCTGAGCGAGTGACAGGCGCGTCCCGCCAAC
CCGCGCCCGGACGGGCAGGGAGGAGCGGCGCGCGGGGCCAACTGCGGCGCGTCTTCCGGCGCCCGCGGAGG
AGGCGAGGGTGGGACGCTGGGCGGAGCCCGAGTTTAGGAAGAGGAGGGGACGGCTGTCATCAATGAAGTCA
TATTCATAATCTAGTCCTCTCTCCCTCTG(transcription start)---exon 1 here
```

METHODS OF IDENTIFYING ACTIVE BRM EXPRESSION-PROMOTING HDAC INHIBITORS

The present application claims priority to U.S. Provisional Application Ser. No. 60/657,603, filed Mar. 1, 2005, herein incorporated by reference in its entirety.

The present application was funded in part with government support under grant number K08 CA092149-02 from the National Institute of Health. The government has certain rights in this invention.

FIELD OF THE INVENTION

The present invention relates to methods and compounds for causing BRM re-expression in cells, such as cancer cells, that have lost BRM expression. In particular, the present invention relates to screening methods for identifying BRM expression-promoting compounds, such as histone deacetylase inhibitors (HDAC) inhibitors; diagnostic methods for determining the suitability of treatment of a candidate subject with a BRM expression-promoting HDAC inhibitor; and therapeutic methods for treating cancer cells in a patient with a BRM expression-promoting HDAC inhibitor. The present invention also relates to BRG1 and BRM diagnostics, methods for increasing a cancer patient's resistance to viral infection, methods for monitoring therapy, and methods for determining the suitability of treatment of a candidate subject with a glucocorticoid compound or retinoid compound.

BACKGROUND OF THE INVENTION

In recent years, "tailor made medicine" is gaining recognition, which takes into consideration individual differences between patients, and a search for a marker to distinguish a cancer against which a pharmaceutical agent is effective from a cancer against which the pharmaceutical agent is ineffective is considered to be necessary. It is an attempt to ethically and medically improve cost performance of medication treatment by administering a pharmaceutical agent to patients after verification in advance of the probability of effect thereof, thereby to enhance efficacy as well as avoid toxicity of the pharmaceutical agent, and to reduce insignificant use of the pharmaceutical agent. In cancer treatment, the development of a method for predicting the efficacy of anticancer agents has been desired, because it can be an important means to bridge the gap between basic study and clinical application.

SUMMARY OF THE INVENTION

The present invention provides screening methods for identifying BRM expression-promoting histone deacetylase (HDAC) inhibitors, diagnostic methods for determining the suitability of treatment of a candidate subject with a BRM expression-promoting HDAC inhibitor, and therapeutic methods for treating cancer cells in a patient with a BRM expression-promoting HDAC inhibitor. The present invention also provides BRG1 and BRM diagnostics, methods for monitoring therapy, methods for increasing a cancer patient's resistance to viral infection, and methods for determining the suitability of treatment of a candidate subject with a glucocorticoid compound or retinoid compound.

In some embodiments, the present invention provides methods of identifying a BRM expression-promoting histone deacetylase inhibitor comprising; a) providing; i) a candidate histone deacetylase inhibitor; and ii) at lease one cell (e.g., a plurality of cells), wherein the cell exhibits reduced BRM protein or BRM mRNA expression; b) contacting the cell with the candidate histone deacetylase inhibitor, and c) measuring BRM protein or BRM mRNA expression exhibited by the cell, or measuring BRM-regulated protein or BRM-regulated mRNA expression from a BRM regulated gene exhibited by the cell, wherein an increase in the BRM protein, BRM mRNA expression, BRM-regulated protein expression, or BRM-regulated mRNA expression exhibited by the cell identifies the candidate histone deacetylase inhibitor as a BRM expression-promoting histone deactylase inhibitor. In certain embodiments, the BRM regulated gene is a gene shown in Table 4.

In certain embodiments, the BRM expression-promoting histone deacetylase inhibitor inhibits a human histone deacetylase protein selected from the group consisting of: HDAC1, HDAC2, HDAC3, HDAC8, and HDAC11. In other embodiments, the BRM expression-promoting histone deacetylase inhibitor inhibits a human histone deacetylase protein selected from the group consisting of: HDAC4, HDAC5, HDAC7, and HDAC9. In other embodiments, the BRM expression-promoting histone deacetylase inhibitor inhibits HDAC1.

In particular embodiments, the BRM expression-promoting histone deacetylase inhibitor specifically inhibits human HDAC1. In some embodiments, the BRM expression-promoting histone deacetylase inhibitor specifically inhibits human HDAC2. In other embodiments, the BRM expression-promoting histone deacetylase inhibitor specifically inhibits human HDAC3. In additional embodiments, the BRM expression-promoting histone deacetylase inhibitor specifically inhibits human HDAC4. In further embodiments, the BRM expression-promoting histone deacetylase inhibitor specifically inhibits human HDAC5. In particular embodiments, the BRM expression-promoting histone deacetylase inhibitor specifically inhibits human HDAC6. In other embodiments, the BRM expression-promoting histone deacetylase inhibitor specifically inhibits human HDAC7. In certain embodiments, the BRM expression-promoting histone deacetylase inhibitor specifically inhibits human HDAC8. In particular embodiments, the BRM expression-promoting histone deacetylase inhibitor specifically inhibits human HDAC9. In other embodiments, the BRM expression-promoting histone deacetylase inhibitor specifically inhibits human HDAC10. In some embodiments, the BRM expression-promoting histone deacetylase inhibitor specifically inhibits human HDAC11.

In particular embodiments, the candidate histone deacetylase inhibitor is identified as a BRM expression-promoting histone deactylase inhibitor, and the method further comprises step d) determining if the BRM protein expressed by the cell after the contacting is active or inactive BRM protein, wherein only the active BRM protein can form a functioning SWI/SNF complex in the cell. In some embodiments, determining if the BRM protein expressed by the cells is active or inactive BRM protein comprises performing an assay to determine if PPARgamma, CD44 or vimentin is up-regulated in the cell. In additional embodiments, the method further comprises step d) determining if CD44 or vimentin is up-regulated in the cell. In other embodiments, the method further comprises step d) measuring retinoblastoma protein growth inhibition in the cell. In some embodiments, the methods further comprises step d) determining if p53, p107, BRCA1 or Farconi's anemia protein are expressed by the cell. In particular embodiments, the BRM protein is determined to be the active BRM protein thereby indicating that the BRM expression-promoting histone deacetylase inhibitor is an active BRM expression-promoting histone deacetylase inhibitor. In other embodiments, the BRM protein is determined to be acetylated and therefore inactive.

In certain embodiments, the cell further exhibits reduced wild-type BRG1 protein or wild-type BRG1 mRNA expression. In some embodiments, the candidate histone deacetylase inhibitor is selected from the group consisting of: a short chain fatty acid, a hydroxamic acid, a tetrapeptide, and a cyclic hydroxamic acid containing peptide. In preferred embodiments, the candidate histone deacetylase inhibitor is selected from the group consisting of: apicidin, butyrates, depsipeptide, FR901228, FK-228, Depudecin, m-carboxy cinnamic acid, bishydroxamic acid, MS-275, N-acetyl dinaline, oxamflatin, pyroxamide, sciptaid, suberoylanilie hydroxamic acid, TPX-HA analogue (CHAP), trapoxin, trichostatin A, and, SB-79872, SB-29201, tabucin, MGCD01013, LBH589, LAQ824, valproate, AN-9, CI-994, MI-1293, valproic acid, HC-toxin, chlamydocin, Cly-2, WF-3161, Tan-1746, analogs of apicidin, benzamide, derivatives of benzamide, hydroxyamic acid derivatives, azelaic bishydroxyamic acid, butyric acid and salts thereof, actetate salts, suberoylanilide hydroxyamide acid, suberic bishydroxyamic acid, m-carboxy-cinnamic acid bishyrdoxyamic acid, or compounds similar to the above (e.g. derivatives of any of these compounds).

In preferred embodiments, the cell is a cancer cell. In some embodiments, the cancer cell is breast cancer cell or a prostate cancer cell (e.g. a hormone insensitive prostate cancer cell). In some embodiments, the cell is from a cell line selected from the group consisting of: H513, H522, H23, H125, A427, SW13, C33A, Panc-1, H1573, and H1299. In certain embodiments, the cell exhibits reduced BRM protein expression. In other embodiments, the cell exhibits reduced BRM mRNA expression. In preferred embodiments, the cell is a human cell. In some embodiments, the cell is part of an animal model (e.g. the cell is part of a tumor growing on or in an animal, such as a mouse or rat).

In certain embodiments, contacting the cell with the candidate histone deacetylase inhibitor is performed in a microtiter plate (e.g. a 96-well plate). In some embodiments, contacting the cell with the candidate histone deacetylase inhibitor is performed in an automated fashion (e.g. for high-throughput screening).

In particular embodiments, the measuring BRM protein or BRM mRNA expression comprises measuring the BRM protein expression. In certain embodiments, the BRM protein expression comprises performing an ELISA assay, a Western Blot, or any other type of protein detection assay. In some embodiments, the protein detection assay employs an anti-BRM antibody.

In additional embodiments, the measuring BRM protein or BRM mRNA expression comprises measuring the BRM mRNA expression. In certain embodiments, measuring the mRNA expression comprises a detection assay selected from the group consisting of: an INVADER assay, a TAQMAN assay, a sequencing assay, a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a rolling circle replication assay, a NASBA assay, a molecular beacon assay, a cycling probe assay, a ligase chain reaction assay, and a sandwich hybridization assay.

In some embodiments, the present invention provides methods for identifying a BRM expression-promoting compound comprising; a) providing; i) a candidate compound; and ii) at least one cell (e.g., plurality of cells), wherein the cell exhibits reduced BRM protein or BRM mRNA expression; b) contacting the cell with the candidate compound, and c) measuring BRM protein or BRM mRNA expression exhibited by the cell, or measuring BRM-regulated protein or BRM-regulated mRNA expression from a BRM regulated gene exhibited by the cell, wherein an increase in the BRM protein, BRM mRNA expression, BRM-regulated protein expression, or BRM-regulated mRNA expression, exhibited by the cell identifies the candidate compound as a BRM expression-promoting compound. In certain embodiments, the BRM regulated gene is a gene shown in Table 4.

In certain embodiments, the candidate compound is identified as a BRM expression-promoting compound, and the method further comprises step d) determining if the BRM protein expressed by the cell after the contacting is active or inactive BRM protein, wherein only the active BRM protein can form a functioning SWI/SNF complex in the cell. In some embodiments, the BRM protein is determined to be the active BRM protein thereby indicating that the BRM expression-promoting compound is an active BRM expression-promoting compound.

In certain embodiments, the present invention provides methods of determining the suitability of treatment of a candidate subject with a BRM expression-promoting histone deacetylase inhibitor, comprising; a) providing a plurality of cancer cells from a candidate subject; b) measuring BRM protein or BRM mRNA expression exhibited by the plurality of cancer cells, or measuring BRM-regulated protein or BRM-regulated mRNA expression from a BRM regulated gene, exhibited by the plurality of cancer cells, in order to determine if the plurality of cancer cells exhibit wild-type or reduced expression of the BRM protein; and c) determining the suitability of treating the candidate subject with a BRM expression-promoting histone deacetylaste inhibitor, wherein the candidate subject is suitable for such treatment if it is determined that the plurality of cells exhibit reduced expression of the BRM protein or the BRM mRNA. In certain embodiments, the BRM regulated gene is a gene shown in Table 4.

In additional embodiments, the present invention provides methods of identifying a candidate subject as suitable for treatment with a BRM expression-promoting histone deacty-lase inhibitor, comprising; a) providing a plurality of cancer cells from a candidate subject; b) measuring BRM protein or BRM mRNA expression exhibited by the plurality of cancer cells, or measuring BRM-regulated protein or BRM-regulated mRNA expression from a BRM regulated gene, exhibited by the plurality of cancer cells, in order to determine if the plurality of cancer cells exhibit wild-type or reduced expression of the BRM protein, and c) identifying the candidate subject as suitable for treatment with a BRM expression-promoting histone deacetylase inhibitor, wherein the identifying comprises finding that the plurality of cells exhibit reduced expression of the BRM protein or the BRM mRNA. In certain embodiments, the BRM regulated gene is a gene shown in Table 4.

In certain embodiments, the plurality of cells further exhibit reduced wild-type BRG1 protein or wild-type BRG1 mRNA expression. In some embodiments, the methods further comprise a step of determining if CD44 or vimentin is up-regulated in the cell.

In particular embodiments, the present invention provides methods of identifying a candidate subject suitable for treatment with a BRM expression-promoting compound, comprising; a) providing a plurality of cancer cells from a candidate subject; b) measuring BRM protein or BRM mRNA expression exhibited by the plurality of cancer cells, and c) identifying the candidate subject as suitable for treatment with a BRM expression-promoting compound, wherein the identifying comprises finding that the plurality of cells exhibit reduced expression of the BRM protein or the BRM mRNA. In certain embodiments, the plurality of cancer cells comprise a biopsy sample from the candidate subject.

In some embodiments, the present invention provides methods of treating cancer cells in a patient comprising; a) identifying a patient comprising a plurality cancer cells, wherein the plurality of cancer cells exhibit reduced BRM protein or BRM mRNA expression; and b) administering a BRM expression-promoting histone deacetylate inhibitor to the patient under conditions such that at least a portion of the plurality of cancer cells are killed. In certain embodiments, the methods further comprise c) administering a glucocorticoid compound or a retinoid compound to the patient. In some embodiments, the glucocorticoid compound is selected from the group consisting of: hydrocortisone, prenisone (deltasone), predrisonlone (hydeltasol), cortisol (hydrocortisone), dexamethasone, triamcinolone, betamethasone, beclomethasone, methylprednisolone, fludrocortisone acetate, deoxycorticosterone acetate (DOCA), and aldosterone. In particular embodiments, the retinoid compound is selected from the group consisting of: retinoid-9-cis retinoic acid, vitamin A, retinaldehyde, retinol, retinoic acid, tretinoin,, iso-tretinoin, and related compounds.

In other embodiments, the present invention provides methods of treating cancer cells in a patient comprising; a) identifying a patient comprising a plurality cancer cells, wherein the plurality of cancer cells are suspected of having reduced BRM protein or BRM mRNA expression; and b) administering a BRM expression-promoting histone deacetylate inhibitor to the patient under conditions such that at least a portion of the plurality of cancer cells are killed. In certain embodiments, the methods fuirther comprise c) administering a glucocorticoid compound or a retinoid compound to the patient. In some embodiments, the glucocorticoid compound is selected from the group consisting of: hydrocortisone, prenisone (deltasone), predrisonlone (hydeltasol), cortisol (hydrocortisone), dexamethasone, triamcinolone, betamethasone, beclomethasone, methylprednisolone, fludrocortisone acetate, deoxycorticosterone acetate (DOCA), and aldosterone. In particular embodiments, the retinoid compound is selected from the group consisting of: retinoid-9-cis retinoic acid, vitamin A, retinaldehyde, retinol, retinoic acid, tretinoin, iso-tretinoin, and related compounds.

In further embodiments, the present invention provides methods of treating cancer cells in a patient comprising; a) identifying a patient comprising a plurality cancer cells, wherein the plurality of cancer cells exhibit reduced BRM protein or BRM mRNA expression; and b) administering a BRM expression-promoting histone deacetylate inhibitor to the patient under conditions such that a least a portion of the plurality of cancer cells express active BRM protein thereby allowing functional SWI/SNF complexes to form in the plurality of cells. In particular embodiments, the BRM expression-promoting histone deacetylase inhibitor is an active BRM expression-promoting histone deacetylase inhibitor. In certain embodiments, the methods further comprise c) administering a glucocorticoid compound or a retinoid compound to the patient.

In some embodiments, the present invention provides methods of treating cancer cells in a patient comprising; a) providing; i) a composition comprising; A) a plurality of BRM proteins, or B) an expression vector configured to express a BRM protein; and ii) a patient comprising a plurality cancer cells suspected of, or having, reduced BRM protein expression; and b) administering the composition to the patient under conditions such that at least a portion of the plurality of cancer cells are killed. In certain embodiments, the expression vector comprises a nucleic acid sequence encoding the BRM protein. In certain embodiments, the methods further comprise c) administering a glucocorticoid compound or a retinoid compound to the patient.

In particular embodiments, the present invention provides methods of treating cancer cells in a patient comprising; a) providing; i) a composition comprising a nucleic acid sequence configured to interfere with expression of a histone deacetylase, and ii) a patient comprising a plurality of cancer cells suspected of, or having, reduced BRM protein expression; and b) administering the composition to the patient under conditions such that at least a portion of the plurality of cancer cells are killed. In certain embodiments, the nucleic acid sequence comprises siRNA or antisense directed against the histone deacetylase.

In some embodiments, the present invention provides methods for determining the suitability of treatment of a candidate subject with a glucocorticoid compound or retinoid compound, comprising; a) providing a plurality of cancer cells from a candidate subject; b) measuring BRM protein or BRM mRNA expression exhibited by the plurality of cancer cells in order to determine if the plurality of cancer cells exhibit wild-type or reduced expression of the BRM protein; and c) determining the suitability of treating the candidate subject with a glucocorticoid compound or retinoid compound, wherein the candidate subject is suitable for such treatment if it is determined that the plurality of cells exhibit wild-type expression of the BRM protein.

In particular embodiments, the present invention provides methods of determining the suitability of treatment of a candidate subject with a glucocorticoid compound or retinoid compound, comprising; a) providing a plurality of cancer cells from a candidate subject; b) measuring BRM protein expression, BRM mRNA expression, or measuring BRM-regulated protein or BRM-regulated mRNA expression of a BRM regulated gene, exhibited by the plurality of cancer cells in order to determine if the plurality of cancer cells exhibit wild-type or reduced expression of the BRM protein; and c) determining the suitability of treating the candidate subject with a glucocorticoid compound or retinoid compound, wherein the candidate subject is suitable for such treatment if it is determined that the plurality of cells exhibit wild-type expression of the BRM protein. In other embodiments, the BRM regulated gene is a gene shown in Table 4.

In certain embodiments, the plurality of cells are determined to exhibit wild-type expression of the BRM protein, and wherein the method further comprises d) administering the glucocorticoid compound or the retinoid compound to the candidate subject. In further embodiments, the plurality of cells are determined to exhibit reduced expression of the BRM protein, and wherein the method further comprises d) administering both a histone deacetylase inhibitor and the glucocorticoid compound or the retinoid compound to the candidate subject. In other embodiments, the plurality of cells are determined to exhibit reduced expression of the BRM protein, and the patient is identified as not suitable for treatment by the glucocorticoid compound or the retinoid compound (e.g. the patient's records are marked as not suitable for treatment with glucocoriticoid or retinoid compounds). In some embodiments, the glucocorticoid compound is selected from the group consisting of: hydrocortisone, prenisone (deltasone), predrisonlone (hydeltasol), cortisol (hydrocortisone), dexamethasone, triamcinolone, betamethasone, beclomethasone, methylprednisolone, fludrocortisone acetate, deoxycorticosterone acetate (DOCA), and aldosterone. In particular embodiments, the retinoid compound is selected from the group consisting of: retinoid-9-cis retinoic acid, vitamin A, retinaldehyde, retinol, retinoic acid, tretinoin,, iso-tretinoin, and related compounds. In particular embodiments, the retinoid compound comprises Bexarotene (e.g. TARGRETIN).

In some embodiments, the present invention provides methods of increasing a cancer patient's resistance to viral infection, wherein the cancer patient comprises a plurality of cancer cells, the method comprising administering a BRM expression-promoting histone deacetylase inhibitor to the cancer patient under conditions such that expression of at least one interferon-induced gene (e.g. as shown in Table 4) is up-regulated in the plurality of cancer cells thereby increasing the cancer patient's resistance to viral infection. In other embodiments, the interferon-induced gene is up-regulated as least 4-fold. In particular embodiments, the BRM expression-promoting histone deacetylase inhibitor is co-administered with a cancer therapy, such as chemotherapy, radiation, surgery, etc.

In certain embodiments, the cancer patient is undergoing treatment with one or more therapeutic compounds that reduce the cancer patient's resistance to viral infection. In other embodiments, the therapeutic compounds is a glucocorticoid compound or a retinoid compound.

In particular embodiments, the present invention provides methods of increasing a cancer patient's resistance to viral infection, wherein the cancer patient comprises a plurality of cancer cells, the method comprising administering i) a plurality of BRM proteins, or ii) an expression vector configured to express a BRM protein, to the cancer patient under conditions such that expression of at least one interferon-induced gene is up-regulated in the plurality of cancer cells thereby increasing the cancer patient's resistance to viral infection. In some embodiments, the cancer patient is undergoing treatment with one or more therapeutic compounds that reduce the cancer patient's resistance to viral infection. In other embodiments, the therapeutic compounds is a glucocorticoid compound or a retinoid compound.

In some embodiments, the present invention provides methods comprising: a) providing a sample comprising a nucleic acid sequence, wherein the nucleic acid sequence comprises at least a portion of a BRM gene or a BRG1 gene; and b) contacting the sample with a nucleic acid detection assay under conditions such that the presence or absence of a SWI/SNF complex formation polymorphism (e.g. a polymorphism that, if present, prevents the successful formation of the SWI/SNF complex) is detected in the BRM gene or the BRG1 gene.

In certain embodiments, the nucleic acid sequence comprises an amplification product. In other embodiments, the amplification product comprises a PCR amplification product. In further embodiments, the nucleic acid detection assay is selected from the group consisting of: a TAQMAN assay, an invasive cleavage assay, a sequencing assay, a polymerase chain reaction assay, a hybridization assay, a microarray assay, a bead array assay, a primer extension assay, an enzyme mismatch cleavage assay, a branched hybridization assay, a rolling circle replication assay, a NASBA assay, a molecular beacon assay, a cycling probe assay, a ligase chain reaction assay, a sandwich hybridization assay, and a Line Probe Assay. In other embodiments, the nucleic acid sequence is derived from a cancer cell. In some embodiments, the cancer cell is from a cancer patient (e.g. from a biopsy of a tumor from a cancer patient).

In further embodiments, the nucleic acid sequence comprises a BRM promoter sequence, and the polymorphism is located at position 741 (as shown in FIG. 5). In other embodiments, the polymorphism at position 741 is a 7 base pair insertion (e.g. TATTTTT (SEQ ID NO:53)). In some embodiments, the nucleic acid sequence comprises at least a portion of the BRG1 gene, and wherein the polymorphism causes an amino acid substitution selected from the group consisting of: P311S; P316S; P319S, and P327S (as shown in FIG. 1B).

In certain embodiments, the nucleic acid sequence is derived from a cancer cell, wherein the nucleic acid sequence comprises a BRM promoter sequence, and the polymorphism is located at position 741. In some embodiments, the cell is determined to be heterozygous or homozygous for the position 741 polymorphism.

In some embodiments, the present invention provides compositions comprising an isolated nucleic sequence that comprises SEQ ID NO:52 (CCCTTTTCattttTATTTTT-TATTTT), or a portion thereof. In particular embodiments, the nucleic acid sequence serves as a positive control for a nucleic acid detection assay configured to detect the presence of the seven base pair insertion in the BRM promoter shown in FIG. 5.

DESCRIPTION OF THE FIGURES

FIG. 1A illustrates the location of each alteration detected in the BRG1 gene with respect to the known domains. Unshaded triangles below the domains represent splicing defects. The circles denote sites of deletions and the hexagons denote the sites of nonsense mutations. FIG. 1B shows missense mutations in a proline-rich region of BRG1. The illustrated region shows a 20-amino-acid region (SEQ ID NO:41) in the N-terminus of the BRG1 gene, which is highly conserved across the human BRG1 and BRM genes, as well as the BRG1 genes of *Xenopus, Drosophila,* and *Danio.* In the cell lines C33A, Panc-1, H1299, and SW13, the conserved prolines in this region are mutated to serines (denoted by arrows).

FIG. 2A shows sequencing chromatographs corresponding to each alteration found in the BRG1 gene. The 69 bp deletion in H1299 is represented by an agarose gel illustrating the truncated PCR product compared to a normal control. Each of the sequence changes appears homozygous, as the unaltered wild-type allele was not detected. FIG. 2B shows the location of the BRG1 splicing defect in the H513, H23, and H1299 cell lines, which resulted in 718, 386, and 250 bp deletions in BRG1, as illustrated in the left column. The junction of each splicing variant is depicted in the chromatograph on the right. The different exons are shaded and labeled. Each aberrantly spliced variant alters the reading frame upstream of the ATPase domain.

FIG. 3A shows BRM protein re-expression in sodium butyrate-treated cell lines. Cells were treated daily with sodium butyrate (5 mM). Total protein was extracted at 4, 12, 24, 36, 50, and 72 hours after the first dosage. Upregulation of BRM with butyrate treatment was detected after 12 hours and reached a plateau between 24 and 48 hours. GAPDH was the loading control. FIG. 3B shows a time course of BRM protein expression after sodium butyrate treatment. Cells were treated with sodium butyrate at a final concentration of 5 mM for three consecutive days. On the fourth day, the medium was changed and cells were harvested at various time points for protein detection. BRM protein levels declined and returned to baseline after 4-5 days. (NaBut=sodium butyrate, un=untreated).

FIG. 5 (SEQ ID NO:42) show the nucleic acid sequence of the human BRM promoter with the seven base insert (SEQ ID NO:53) at position 741 underlined.

DEFINITIONS

Figure 1:
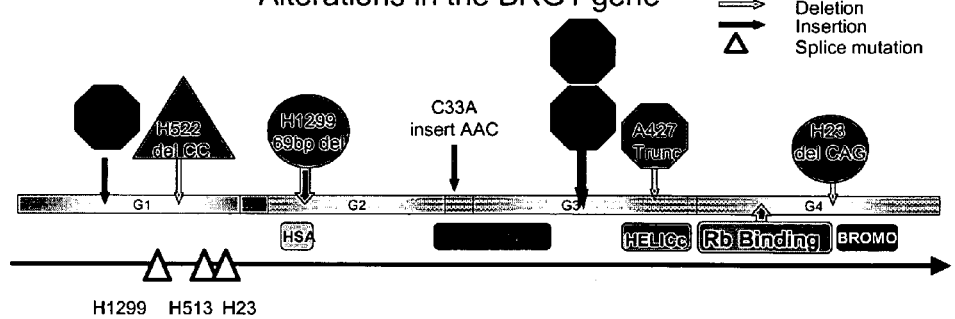
FIG. 1 shows the location of various BRG1 mutations.
Figure 1:
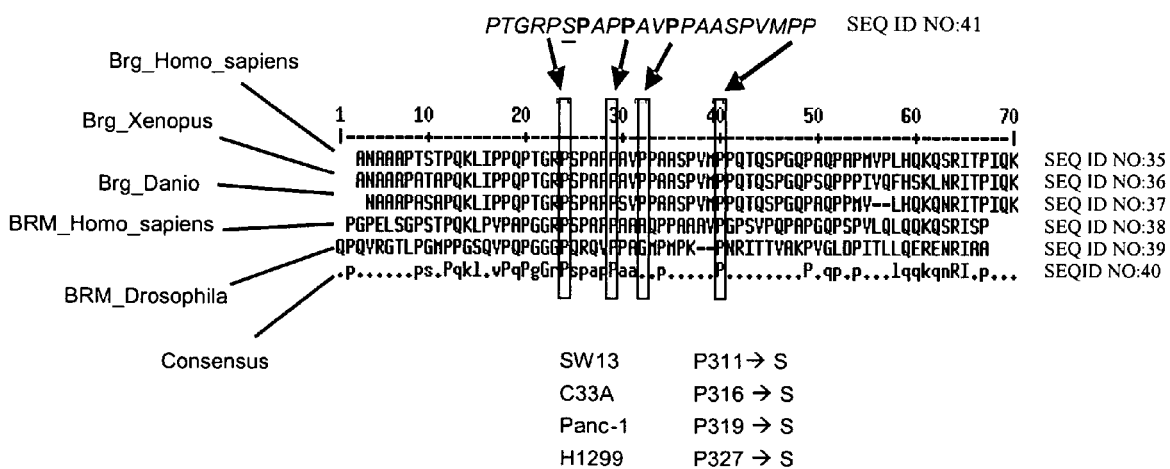

To facilitate an understanding of the invention, a number of terms are defined below.

As used herein, the terms "subject" and "patient" refer to any animal, such as a mammal like a dog, cat, bird, livestock, and preferably a human. Specific examples of "subjects" and "patients" include, but are not limited to, individuals with cancer, such as breast cancer or prostate cancer.

The term "wild-type" refers to a gene or protein that has the characteristics of that gene or gene product when isolated from a naturally occurring source. A wild-type gene or protein is that which is most frequently observed in a population and is thus arbitrarily designed the "normal" or "wild-type" form of the gene. In contrast, the term "variant" refers to a gene or protein that displays modifications in sequence and/or functional properties (i.e., altered characteristics) when compared to the wild-type gene or gene product.

As used herein, the term "antisense" is used in reference to RNA sequences that are complementary to a specific RNA sequence (e.g., mRNA). Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the phrase "BRM regulated gene" refers to any gene who's mRNA and/or protein expression is increased in a cell when BRM mRNA or protein expression is increased in said cell. For example, when BRM expression is increased in a cell through contact with an HDAC inhibitor, any gene who's expression is also increased qualifies as a BRM regulated gene. Examples of BRM regulated genes include, but are noted limited to, CD44, E-cadherin, SPARK, LBH, CEA CAM-1, S100A2, RARR3, GADD45a, an interferon induced gene, and genes shown in Table 4.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual,* Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The phrase "candidate compound" refer to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention.

As used herein, the terms "histone deacetylase" and "HDAC" are intended to refer to any one of a family of enzymes that remove acetyl groups from the epsilon-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11.

The term "histone deacetylase inhibitor" or "inhibitor of histone deacetylase" is used to identify a compound which is capable of interacting with a histone deacetylase and inhibiting its enzymatic activity. Inhibiting histone deacetylase enzymatic activity means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%. Preferably, such inhibition is specific, such that the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

As used herein a "BRM expression-promoting histone deacetylase inhibitor" is a histone deacetylase inhibitor that is able to cause a cell with reduced BRM protein or mRNA expression to begin expressing BRM protein or mRNA, or increase the level of expression or BRM protein or mRNA (e.g. by at least 20%), when contacted with that cell.

As used herein, a histone deacetylase inhibitor "specifically inhibits" a given HDAC when the inhibitor only inhibits the function of the given HDAC in a cell, and not any of the other HDACs. For example, if a histone deacetylase inhibitor "specifically inhibits" HDAC2 in a human cell, this inhibitor, when contacted with a cell, would not inhibit HDACs 1, 3, 4, 5, 6, 7, 8, 9, 10 and 11.

As used herein, a cell exhibits "reduced BRM protein or BRM mRNA expression" when the cell either exhibits no BRM protein or mRNA expression, or the level of BRM protein or BRM mRNA expression is less than 75 percent of that wild type level found in cells of the same type (e.g. cells of the same type that are not cancerous).

As used herein, a cell exhibits "reduced wild-type BRG1 protein or wild-type BRG1 mRNA expression" when the cells exhibits no wild-type BRG1 protein or mRNA expression (e.g. all of the BRG1 protein expressed is mutant form), or the level of wild-type BRG1 protein or wild-type BRG1 mRNA is less than 75 percent of the wild-type level found in cells of the same type (e.g. cells of the same type that are not cancerous).

As used herein, the term "suitable for treatment with a BRM expression-promoting histone deacetylase inhibitor" when used in reference to a candidate subject refers to subjects who are more likely to benefit from such treatment than a subject selected randomly from the population. An example of such a candidate subject is one who has been determined to have cancer cells with reduced BRM expression.

DESCRIPTION OF THE INVENTION

The present invention provides screening methods for identifying BRM expression-promoting histone deacetylase (HDAC) inhibitors, diagnostic methods for determining the suitability of treatment of a candidate subject with a BRM expression-promoting HDAC inhibitor, and thereapeutic methods for treating cancer cells in a patient with a BRM expression-promoting HDAC inhibitor. The present invention also relates to BRG1 and BRM diagnostics, methods for increasing a cancer patient's resistance to viral infection, and methods for determining the suitability of treatment of a candidate subject with a glucocorticoid compound or retinoid compound. For convenience, the description of the invention is provided below under the following headings: I) SWI/SNF Complex; II) Histone Deacetylases; III) Histone Deacetylase Inhibitors; IV) Screening Methods; V) Therapeutic Methods and Compositions; VI) Treating and Preventing Viral Infection; and VII) Detecting SWI/SNF Related Polymorphisms.

I. SWI/SNF Complex

Chromatin remodeling plays an essential role in regulating gene expression. By controlling which areas of chromatin are open or condensed, cells are limited to which genes they can express. Along the chromatin, histones are marked by the addition of acetyl or methyl groups. These secondary modifications to histones provide a code (a histone code) that determines which specific areas of the chromatin will be opened or condensed. This histone code is maintained and read by a complex array of multimeric proteins collectively called chromatin remodeling complexes. Restricting the accessibility of the DNA in this way limits the function of transcription factors and key cellular proteins and is used by normal cells to maintain differentiation and control growth. However, cancer cells can escape these restraints by disrupting the function of these chromatin remodeling complexes. The SWI/SNF complex is one such important chromatin remodeling complex that is involved in gene regulation and whose dysregulation has been shown to contribute to cancer development.

The SWI/SNF complex contains 9-12 proteins and provides direct access to DNA by shifting the position of the histones (Wang et al., Curr. Top. Microbiol. Immunol., 2003, 274:143-69, herein incorporated by reference). It was first linked to tumorigenesis with the finding that the SWI/SNF subunit, BAF47, is a bona fide tumor suppressor protein. The loss of this protein has been shown to be a key event in the development of rhabdoid sarcoma, a lethal pediatric tumor. In cell lines derived from these tumors, re-expression of the BAF47 proteins causes pronounced growth arrest and differentiation. In heterozygous BAF47 knock-out mice, sarcoma-like tumors develop, while homozygous inactivation of this protein is highly tumorigenic, yielding tumors within weeks.

In addition to BAF47, other SWI/SNF subunits are now known to be altered in human tumors. It has been found that the ATPase subunit, BRM, is lost in 30-40% of lung cancer cell lines (Reisman et al., Oncogene, 2002, 21(8):1196-207, herein incorporated by reference) and 10-20% of primary lung cancers (Reisman et al., Cancer Res., 2003, 63(3), 560-6, herein incorporated by reference). This subunit is essential, as its loss disrupts function of the SWI/SNF complex. When BRM expression is restored in cancer cell lines, a progressive growth arrest ensues and the cells adopt a flattened, differentiated phenotype. This observation supports the role of the SWI/SNF complex in facilitating growth-controlling pathways. In addition, alterations to the SWI/SNF complex appear to occur in a number of tumor types. It has been found by immunostaining tissue microarrays (TMAs) that the expression of BRM is lost in 5-15% of esophageal, ovarian, prostate, bladder, head/neck tumors and lung cancer.

Which pathways are selectively disrupted when the SWI/SNF complex is abrogated is not currently known. But a variety of key cellular proteins are known to rely upon SWI/SNF activity for their function. For example, the retinoic acid receptor (RAR) and proxisome proliferative receptor gamma (PPAR-γ), which oppose cancer development, require the SWI/SNF complex. In addition, tumor suppressor proteins such as p53, p107, and Rb (retinoblastoma protein) have also been functionally linked to the SWI/SNF complex, as have proteins involved in DNA repair, including BRCA1 and Fanconi's anemia protein. Thus, loss of the BRM protein will strip away many of the mechanisms that are responsible for the control and fidelity of normal proliferation. In mammalian cells, numerous transcription factors, including Ets-2, ELKF, AP-1 and Stat-3 require the SWI/SNF complex. Through these and other interactions, the SWI/SNF complex is important for the normal expression of a variety of genes. In yeast, the Swi/Snf complex controls the expression of approximately 5-7% of the yeast genome.

While not limited to any mechanism, it is believed that restoring BRM expression in accordance with the methods and compositions of the present invention (e.g. by inhibiting certain HDACs) has clinical applications. SWI/SNF activity is required for the function of both RAR and PPARγ. Since agonists of RAR and PPARγ are clinically utilized as antitumor agents, restoring BRM could, in certain embodiments, increase the number of patients who could benefit from these drugs. Moreover, it has been shown that BRM expression is lost in a subset of both prostate and breast cancers. As both estrogen and androgen receptors also functionally require the SWI/SNF complex, BRM re-expression could be used to allow for the restoration of hormone sensitivity to breast and prostate cancer patients who have become refractory to anti-hormone therapy. In addition, the loss of BRM expression and SWI/SNF activity may herald more aggressive forms of cancers. The proteins involved in DNA repair, such as p53, BRCA1 and Fanconi's anemia, and in cell adhesion, such as integrins, CD44 and E-cadherin, are also linked to the SWI/SNF complex. Thus re-expression of BRM by the methods and compositions of the present invention, in some embodiments, could be used to thwart neoplastic development by restoring DNA repair mechanisms and reducing tumor metastatic potential. Furthermore, restoring BRM expression has antiproliferative effects. While not necessary to understand to practice the present invention this may be one mechanism by which HDAC inhibitors are inhibitory and have clinical efficacy.

II. Histone Deacetylases (HDACs)

Nucleosomes, the primary scaffold of chromatin folding, are dynamic macromolecular structures, influencing chromatin solution conformations. The nucleosome core is made up of histone proteins, H2A, HB, H3 and H4. Histone acetylation causes nucleosomes and nucleosomal arrangements to behave with altered biophysical properties. The balance between activities of histone acetyl transferases (HATs) and deacetylases (HDACs) determines the level of histone acetylation. Acetylated histones cause relaxation of chromatin and activation of gene transcription, whereas deacetylated chromatin generally is transcriptionally inactive.

Eleven different HDACs have been cloned from vertebrate organisms. The first three human HDACs identified were HDAC 1, HDAC 2 and HDAC 3 (termed class I human HDACs), and HDAC 8 has been added to this list. More recently class II human HDACs, HDAC 4, HDAC 5, HDAC 6, HDAC 7, HDAC 9, and HDAC 10 have been cloned and identified. Additionally, HDAC 11 has been identified but not yet classified as either class I or class II. All share homology in the catalytic region. HDACs 4, 5, 7, 9 and 10 however, have a unique amino-terminal extension not found in other HDACs. This amino-terminal region contains the MEF2-binding domain. HDACs 4, 5 and 7 have been shown to be involved in the regulation of cardiac gene expression and in particular embodiments, repressing MEF2 transcriptional activity. The exact mechanism in which class II HDAC's repress MEF2 activity is not completely understood. One possibility is that HDAC binding to MEF2 inhibits MEF2 transcriptional activity, either competitively or by destabilizing the native, transcriptionally active MEF2 conformation. It also is possible that class II HDAC's require dimerization with MEF2 to localize or position HDAC in a proximity to histones for deacetylation to proceed.

III. Histone Deacetylase Inhibitors

The present invention is not limited by the type of histone deacetylase inhibitor that is used with the methods and composition of the present invention. A variety of inhibitors for histone deacetylases have been identified. The proposed uses range widely, but primarily focus on cancer therapy. Compounds which inhibit histone deacetylase (HDACs) have been shown to cause growth arrest, differentiation and/or apoptosis of many different types of tumor cell in vitro and in vivo. HDAC inhibitors generally fall into four general classes: 1) short-chain fatty acids (e.g., 4-phenylbutyrate and valproic acid); hydroxamic acids (e.g., SAHA, Pyroxamide, trichostatin A (TSA), oxamflatin and CHAPs, such as, CHAPI and CHAP 31); 3) cyclic tetrapeptides (e.g., Trapoxin A and Apicidin); 4) benzamides (e.g., MS-275); and other compounds such as SCRIPTAID. Examples of such compounds can be found in U.S. Pat. Nos. 5,369,108; 5,700,811; and 5,773,474; 5,055,608; and 5,175,191; as well as, Yoshida, M., et al., Bioassays 17, 423-430 (1995), Saito, A., et al., PNAS USA 96, 4592-4597, (1999), Furamai R. et al., PNAS USA 98 (1), 87-92 (2001), Komatsu, Y., et al., Cancer Res. 61(11), 4459-4466 (2001), Su, G. H., et al., Cancer Res. 60, 3137-3142 (2000), Lee, B. I. et al., Cancer Res. 61(3), 931-934, Suzuki, T., et al., J. Med. Chem. 42(15), 3001-3003 (1999) and published PCT Application WO 01/18171 the entire content of all of which are hereby incorporated by reference in their entireties.

HDACs can be inhibited a number of different ways such as by proteins, peptides, and nucleic acids (including antisense and RNAi molecules). Methods are widely known to those of skill in the art for the cloning, transfer and expression of genetic constructs, which include viral and non-viral vectors, and liposomes. Viral vectors include adenovirus, adeno-associated virus, retrovirus, vaccina virus and herpesvirus. Example of certain RNAi type inhibitors are provided in Glaser et al., Biochem. and Biophys. Res. Comm., 310:529-36, 2003, herein incorporated by reference in its entirety). Other HDAC inhibitors are small molecules. Perhaps the most widely known small molecule inhibitor of HDAC function is Trichostatin A, a hydroxamic acid. It has been shown to induce hyperacetylation and cause reversion of ras transformed cells to normal morphology and induces immunsuppression in a mouse model. It is commercially available from BIOMOL Research Labs, Inc., Plymouth Meeting, Pa.

The following references all describe HDAC inhibitors that may find use in the present invention: U.S. Pat. Nos. 6,706,686; 6,541,661; 6,638,530; 6,541,661; U.S. Pat. Pub. 2004/0077698; EP1426054; U.S. Pat. Pub. 2003/0206946; U.S. Pat. No. 6,825,317; U.S. Pat. Pub. 2004/0229889; WO0215921; U.S. Pat. No. 5,993,845; U.S. Pat. Pub. 2004/0224991; WO04046094; U.S. Pat. Pub. 2003/0129724; U.S. Pat. No. 5,922,837; WO04113336; U.S. Pat. Pub. 2004/0132825; U.S. Pat. Pub. 2005/0032831; U.S. Pat. Pub. 2004/021486; U.S. Pat. No. 6,784,173; U.S. Pat. Pub. 2003/0013757; U.S. Pat. Pub. 2002/0103192; and U.S. Pat. Pub. 2002/0177594—all of which are herein incorporated by reference in their entireties as if fully reproduced herein.

Examples of certain preferred HDAC inhibitors includes, but is not limited to, trichostatin A, trapoxin A, trapoxin B, HC-toxin, chlamydocin, Cly-2, WF-3161, Tan-1746, apicidin, analogs of apicidin, benzamide, derivatives of benzamide, hydroxyamic acid derivatives, azelaic bishydroxyamic acid, butyric acid and salts thereof, actetate salts, suberoylanilide hydroxyamide acid, suberic bishydroxyamic acid, m-carboxy-cinnamic acid bishyrdoxyamic acid, oxamflatin, depudecin, tabucin, valproate, AN-9, CI-994, FR901228, and MS-27-275. Alternatively, the agent can be a therapeutically effective oligonucleotide that inhibits expression or function of histone deacetylase, or a dominant negative fragment or variant of histone deacetylase. Other preferred compounds includes those from MethylGene Corp., such as Compound MGCDO103, and compounds LBH589 and LAQ824 from Novartis (see Qian et al., Clin. Cancer. Res., 2006, 12(2):634-42; and Remiszewski et al., J. Med. Chem., 2003, 46(21): 4609-24), both of which are herein incorporated by reference. Other preferred compounds are from Chroma therapeutics, such as Compound CHR-2504. Table 1 provides additional HDAC inhibitors and the sensitivity known HDACs to these HDAC inhibitors.

IV. Screening Methods

The present invention provides methods for screening compounds, preferably HDAC inhibitors, to identify compounds that cause BRM expression. The screening methods are not limited by the types of cells, but preferably employ cells that have reduced or absent BRM expression. Preferably the cells employed not only have reduced BRM expression, but also have reduced levels of BRG1 expression (i.e. reduced wild-type BRG1 protein or mRNA expression levels).

In preferred embodiments, the cells are contacted with a candidate compound (e.g. a HDAC inhibitor) and the expression of BRM mRNA and/or BRM protein is detected to determine if the compound causes an increase in such BRM expression. The host cells may already contain molecules that indicate the level of BRM mRNA expression or BRM protein expression such that no additional reagents need to be added to the cells. For example, the cells may be stably transfected with nucleic acid sequences for mRNA detection assays such as at least one of the following assays: the INVADER assay, a TAQMAN assay, a sequencing assay, a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a rolling circle replication assay, a NASBA assay, a molecular beacon assay, a cycling probe assay, a ligase chain reaction assay, and a sandwich hybridization assay. Alternatively, one of these mRNA detection assays can be added to the cells after exposure to the candidate compound to determine if the compound caused an increase in BRM mRNA expression.

Responses of cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and

TABLE 1

The sensitivity of the known HDACs to various HDAC inhibitors

| | Butyrate | Trichostatin | FR901228 | Trapoxin | MS-275 | Scriptaid | SB-79872 | SB-29201 | Valpoic Acid | MI-1293 |
|---|---|---|---|---|---|---|---|---|---|---|
| Class 1 | | | | | | | | | | |
| HDAC1 | Yes $IC_{50}$~0.3 mM | Yes $IC_{50}$~0.3 uM | Yes | Yes $IC_{50}$~0.01 uM | Yes $IC_{50}$~0.3 uM | Yes $IC_{50}$~0.6 uM | No | Yes $IC_{50}$~1.5 uM | yes | yes |
| HDAC2 | | | | | | | | | yes | yes |
| HDAC3 | Yes $IC_{50}$~0.3 mM | Yes $IC_{50}$~0.3 uM | Yes | Yes $IC_{50}$~0.1 uM | Yes $IC_{50}$~8 uM | Yes $IC_{50}$~0.6 uM | No | No | | |
| HDAC8 | Yes | Yes $IC_{50}$~0.3 uM | | No: $IC_{50}$ > 100 | Yes $IC_{50}$~1.0 uM | | Yes $IC_{50}$~0.5 uM | No | | |
| HDAC11 | | | | Yes $IC_{50}$~0.1 uM | | | | | | |
| Class 2 | | | | | | | | | | |
| HDAC4 | | Yes $IC_{50}$~.01 uM | weak | | | | | | | |
| HDAC5 | | Yes | | | | | | | | |
| HDAC6 | No | Yes | weak | No | | | | | | |
| HDAC7 | | Yes | | | | | | | | |
| HDAC9 | | Yes | | | | | | | | |
| HDAC10 | No | Yes $IC_{50}$~.01 uM | | No | | | | | | |
| Class 3 | Resistance | Resistance | | | | | | | | | expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

In certain embodiments, the presence of BRM protein is detected in the cells after being contacted with a candidate compound. Techniques for measuring such expression levels are known in the art. One preferred technique is an ELISA assay that could employ antibodies directed to BRM to indicate the level of BRM expression after the cell is contacted with a candidate compound. Examples of anti-BRM antibodies include, but are not limited to, the anti-BRM monoclonal antibody distributed by BD Biosciences (BD Biosciences, Franklin Lakes, N.J.), and two anti-BRM polyclonal antibodies from Santa Cruz Biotechnology (Santa Cruz, Calif.).

In addition to selecting known HDAC inhibitors as the compound to test, one may also employ libraries of various test compounds. The test compounds can be obtained, for example, using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

In preferred embodiments, HDAC inhibitors are identified that are BRM expression-promoting histone deacetyalse inhibitors. In preferred embodiments, such inhibitors that only inhibit one of the known 11 HDACs, but still promote BRM expression, are identified. In order to identify such inhibitors, various methods may be used. For example, RNAi may be used to selectively inhibit each of the 11 HDACs (e.g. one at a time) to determine which HDAC or HDACs can be inhibited and lead to BRM expression (e.g. lead to BRM expression in a cell deficient in BRM expression).

In certain preferred embodiments, screening methods are employed to identify HDAC inhibitors that promote BRM expression, such that the BRM expressed is able to form part of a functioning SWI/SNF complex. For example, methods are employed that identify HDAC inhibitors that do not also induce the acetylation of BRM (as acetylation of BRM causes BRM to be inactivated). In certain embodiments, CD44 and vimentin are detected as indicators of active BRM expression. In other embodiments, Rb growth inhibition is detected. For example, to measure Rb growth inhibition, one could co-transfect MS-Rb, a constitutively active form of RB, in conjunction with a given HDAC inhibitor (e.g. a particular small molecule or siRNA). After 48 hours, transfected cells could be pulsed with BrdU for 24 hours and growth inhibition could be measured by immunostaining for BrdU incorporation.

V. Therapeutic Methods and Compositions

In certain embodiments, the present invention provides therapeutic methods and compositions for treating a subject with a compound that promotes BRM expression in cancer cells in the patient that have. reduced BRM expression. In preferred embodiments, the therapeutic compound is a HDAC inhibitor. In other preferred embodiments, the therapeutic compound is an HDAC inhibitor that specifically inhibits only one HDAC. In particularly preferred embodiments, the HDAC inhibitor promotes expression of active BRM in cancer cells. In other embodiments, BRM peptides or nucleic acids sequences encoding BRM are administered to a patient.

The therapeutic compounds, peptides and nucleic acids of the present invention may be administered alone or in combination with at least one other agent, such as a stabilizing compound, and may be administered in any sterile, biocompatible pharmaceutical carrier, including, but not limited to, saline, buffered saline, dextrose, and water. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy methods.

As is well known in the medical arts, dosages for any one patient depends upon many factors, including the patient's size, body surface area, age, the particular compound to be administered, sex, time and route of administration, general health, and interaction with other drugs being concurrently administered.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated. In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of NPHP4, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range. With respect to HDAC inhibitors specifically, in certain embodiments, it is preferably administered at a sufficient dosage to attain a blood level of the inhibitor from about 0.01 M to about 100 M, more preferably from about 0.05 M to about 50 M, still more preferably from about 0.1 M to about 25 M, and still yet more preferably from about 0.5 M to about 25 M. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain embodiments, the therapeutic is a nucleic acid sequence encoding a HDAC inhibitor (e.g. siRNA, see, Glaser et al., Biochemical and Biophysical Res. Comm., 310: 529-36, 2003, herein incorporated by reference) or a nucleic acid sequence encoding BRM. In certain embodiments, the nucleic acid sequence is part of a vector such as an Adenovirus or Adeno-Associate virus such that the vector can express the nucleic acid sequence in the cells of a patient (e.g. cancer cells of a patient that are deficient for BRM expression).

VI. Treating and Preventing Viral Infection

In certain embodiments, the present invention provides methods and composition for treating viral infections, particularly in cancer patients. It is contemplated that many cancer patients actually die or get severely sick from cancer induced viral infections, rather than from their cancer, as their cancer leaves them exposed to such viral infections. Indeed, a large percent of cancer patients (e.g. 5% or more) may get sick or die from viral infections as a result of their cancer. While the cause of death may be officially noted as cancer, the true cause is actually viral infection that resulted from the cancer. The present invention addresses this widespread problem by treating cancer patients to reduce their risk of cancer induced viral infection, or to help treat on-going viral infections that resulted from having cancer. For example, in some embodiments, a cancer patient may have cancer cells that have reduced expression of BRM and/or interferon induced genes. Such reduced expression, it is contemplated, leaves the patient exposed to greatly increased risk of viral infection that may ultimately lead to severe sickness or death. In order to reduce this risk of viral infection, or treat an on-going viral infection, a patient is treated with compounds that increase the expression of at least one and preferably more interferon induced genes. The present invention is not limited by the type of compound employed. Exemplary interferon induced genes that may be up-regulated to treat cancer induced viral infection are shown in Table 4. In certain embodiments, the patient is treated with a histone deacetylase inhibitor in order to increase the expression of one or more interferon induced genes. In other embodiments, the patient is treated with BRM proteins or nucleic acid sequences that direct the expression of BRM proteins.

VII. Detecting SWI/SNF Related Polymorphisms

In certain embodiments, the present invention provides compositions and methods for detecting polymorphisms, such as SNPs and insertions, that provide information on whether SWI/SNF complexes will properly form or not in a given cell or population of cells. In certain embodiments, polymorphisms in the BRM gene (including the promoter) are detected. In other embodiments, polymorphisms in the BRG1 gene are detected. In some embodiments, nucleic acid detection assays are used to determine the presence or absence of polymorphisms in the BRM gene (including the promoter), such as position 741 insertions in the promoter. In additional embodiments, nucleic acid detection assays are used to determine the presence or absence of polymorphisms in the BRG1 gene, such as P311S; P316S; P319S, and P327S or other polymorphisms shown in FIG. 1. The present invention is not limited by the type of nucleic acid detection assay used to detect such polymorphisms. Detailed below are exemplary nucleic acid detection assays.

1. Direct Sequencing Assays

In some embodiments of the present invention, BRM and BRG1 polymorphisms are detected using a direct sequencing technique. In these assays, nucleic acid samples are first isolated from a sample from a subject using any suitable method. In some embodiments, the region of interest is cloned into a suitable vector and amplified by growth in a host cell (e.g., a bacteria). In other embodiments, nucleic acid in the region of interest is amplified using PCR. Following amplification, nucleic acid in the region of interest is sequenced using any suitable method, including but not limited to manual sequencing using radioactive marker nucleotides, or automated sequencing. The results of the sequencing are displayed using any suitable method. The sequence is examined and the presence or absence of BRM or BRG1 polymorphisms are located.

2. PCR Assays

In some embodiments of the present invention, BRM and BRG1 polymorphisms are detected using a PCR-based assay. In some embodiments, the PCR assay comprises the use of oligonucleotide primers that hybridize only to a given polymorphic sequence and primers that will not hybridize to the polymorphic sequence. Both sets of primers are used to amplify a sample of DNA. If only the polymorphic specific primers result in a PCR product, then the patient has the particular polymorphism.

3. Fragment Length Polymorphism Assays

In some embodiments of the present invention, BRM and BRG1 polymorphisms are detected using a fragment length polymorphism assay. In a fragment length polymorphism assay, a unique DNA banding pattern based on cleaving the DNA at a series of positions is generated using an enzyme (e.g., a restriction enzyme). Nucleic acid fragments from a sample containing a particular polymorphism will have a different banding pattern than those sequences not containing that particular polymorphism.

4. Hybridization Assays

In certain embodiments of the present invention, BRM and BRG1 polymorphisms are detected with a hybridization assay. In a hybridization assay, the presence of absence of a particular polymorphism may be determined based on the ability of the nucleic acid from the sample to hybridize to a complementary nucleic acid molecule (e.g., an oligonucleotide probe). A variety of exemplary hybridization assays using a variety of technologies for hybridization and detection are described below.

a. Direct Detection of Hybridization

In some embodiments, hybridization of a probe to the sequence of interest is detected directly by visualizing a bound probe (e.g., a Northern or Southern assay; See e.g., Ausabel et al. (eds.), Current Protocols in Molecular Biology, John Wiley & Sons, NY [1991]). In these assays, nucleic acid is isolated from a sample. The DNA or RNA is then separated (e.g., on an agarose gel) and transferred to a membrane. A labeled (e.g., by incorporating a radionucleotide) probe or probes specific for a BRM or BRG1 polymorphism (e.g. 7 base pair insertion at position 741 of the BRM promoter) is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, BRM and BRG1 related polymorphisms are detected using a DNA chip hybridization assay. In this assay, a series of oligonucleotide probes are affixed to a solid support. The oligonucleotide probes are designed to be unique to a given sequence. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high density arrays of oligonucleotide probes affixed to a "chip." Probe arrays are manufactured by Affymetrix's light directed chemical synthesis process, which combines solid phase chemical synthesis with photolithographic fabrication techniques employed in the semiconductor industry. Using a series of photolithographic masks to define chip exposure sites, followed by specific chemical synthesis steps, the process constructs high density arrays of oligonucleotides, with each probe in a predefined position in the array. Multiple probe arrays are synthesized simultaneously on a large glass wafer. The wafers are then diced, and individual probe arrays are packaged in injection molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for positions BRM or BRG1 polymorphisms are affixed to the chip using Protogene's technology. The chip is then contacted with the sample potentially containing nucleic acid sequences that may contain such polymorphisms. Following hybridization, unbound DNA is removed and hybridization is detected using any suitable method (e.g., by fluorescence de-quenching of an incorporated fluorescent group).

In yet other embodiments, a "bead array" is used for the detection of BRM and BRG1 polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self assemble into an array. Each fiber optic bundle contains thousands to millions of individual fibers depending on the diameter of the bundle. The beads are coated with an oligonucleotide specific for particular BRM or BRG1 polymorphisms. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (e.g., INVADER assay, Third Wave Technologies; See e.g., U.S. Pat. Nos. 5,846,717; 5,985,557; 5,994,069; 6,001,567; 6,913,881; and 6,090,543, WO 97/27214, WO 98/42873, Lyamichev et al., Nat. Biotech., 17:292 (1999), Hall et al., PNAS, USA, 97:8272 (2000), each of which is herein incorporated by reference in their entirety for all purposes). The INVADER assay detects specific DNA and RNA sequences by using structure specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5' end labeled with a fluorescent dye that is quenched by a second dye or other quenching moiety. Upon cleavage, the de-quenched dye-labeled product may be detected using a standard fluorescence plate reader, or an instrument configured to collect fluorescence data during the course of the reaction (i.e., a "real-time" fluorescence detector, such as an ABI 7700 Sequence Detection System, Applied Biosystems, Foster City, Calif.).

In an embodiment of the INVADER assay used for detecting SNPs, two oligonucleotides (a primary probe specific either for a particular base at the SNP, and an INVADER oligonucleotide) hybridize in tandem to the target nucleic acid to form an overlapping structure. A structure-specific nuclease enzyme recognizes this overlapping structure and cleaves the primary probe. In a secondary reaction, cleaved primary probe combines with a fluorescence-labeled secondary probe to create another overlapping structure that is cleaved by the enzyme. The initial and secondary reactions can run concurrently in the same vessel. Cleavage of the secondary probe is detected by using a fluorescence detector, as described above. The signal of the test sample may be compared to known positive and negative controls.

5. Other Detection Assays

Additional detection assays that are produced and utilized using the systems and methods of the present invention include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Bamay Proc. Natl. Acad. Sci USA 88, 189-93 (1991)); and sandwich hybridization methods (e.g., U.S. Pat. No. 5,288,609, herein incorporated by reference in its entirety).

6. Mass Spectroscopy Assay

In some embodiments, a MassARRAY system (Sequenom, San Diego, Calif.) is used to detect BRM and BRG1 related polymorphisms (See e.g., U.S. Pat. Nos. 6,043,031; 5,777,324; and 5,605,798; each of which is herein incorporated by reference). DNA is isolated from blood samples using standard procedures. Next, specific DNA regions containing the region of interest (e.g, about 200 base pairs in length) are amplified by PCR. The amplified fragments are then attached by one strand to a solid surface and the non immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI TOF (Matrix Assisted Laser Desorption Ionization Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

8. Exemplary BRM Promoter Probes, Primers, and Compositions

In certain embodiments, the present invention provides probes and primers specific for the BRM promoter (e.g. as shown in FIG. 5). In preferred embodiments, the probes and primers are useful in detecting a polymorphism at position 741, and particularly the seven base pair insert TATTTTT (SEQ ID NO:53) shown in FIG. 5. Exemplary probes and primers, that could be used with a nucleic acid detection assay such as those discussed above, include nucleic acids comprising, or consisting of, the following sequences:

```
CTTTTCtattttTATTTTT;       (SEQ ID NO:44)

CCTTTTCtattttTATTTTT;      (SEQ ID NO:45)

CTTTTCtattttTATTTTT;       (SEQ ID NO:46)

CCTTTTCtattttTATTTTTT;     (SEQ ID NO:47)

tattttTATTTTTTATT;         (SEQ ID NO:48)

tattttTATTTTTTATTTT;       (SEQ ID NO:49)

GCCCGCCTCCCTTTTCtattttt;   (SEQ ID NO:50)
and

CGCCTCCCTTTTCtattttt.      (SEQ ID NO:51)
```

In certain embodiments, the present invention provides PCR primers for amplifying the region surrounding the seven base pair insert shown in FIG. 5. PCR-primers can be designed by generating at least one primer upstream of the seven base pair insert and at least one primer downstream of the seven base pair insert. In particular embodiments, nested PCR primers are generated (e.g. two upstream primers and two downstream primers).

In some embodiments, the present invention provides compositions comprising an isolated nucleic sequence that comprises SEQ ID NO:52 (CCCTTTTCattttTATTTTT-TATTTT). Such nucleic acid sequence can be used, for example, as a positive control target in a nucleic acid detection assay designed to detect the seven base pair insert shown in FIG. 5 or as a probe for detecting this seven base pair insert.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); C (degrees Centigrade); and Sigma (Sigma Chemical Co., St. Louis, Mo.).

EXAMPLE 1

BRM and BRG1 Sequencing in BRM+BRG1 Deficient Cells Lines

This example describes sequencing BRG1 and BRM sequences in cells lines deficient in BRG1 and BRM protein expression. By western blotting, 10 cell lines were identified which lack BRG1 and/or BRM expression. The characteristics of these cells lines are provided in Table 1.

TABLE 1

| Cell line | Tissue | Major alteration | Exon(s) | Predicted effect | Other alterations |
|---|---|---|---|---|---|
| A427 | Lung | Homozygous deletion | 22 | Truncation | |
| NCI-H23 | Lung | Altered splicing | 5-8 | Frameshift | Ser 1477 deletion |
| NCI-H125 | Lung | G → T | 21 | Glu 1056 → STOP | |
| NCI-H513 | Lung | Altered splicing G → T | 4-6 | Frameshift: Glu 1056 → STOP | |
| NCI-H522 | Lung | 2 bp deletion | 5 | Frameshift | |
| NCI-H1299 | Lung | Altered splicing | 3 & 4 | Frameshift/ Truncation | 69 bp deletion exon 10 P327 → S |
| NCI-H1573 | Lung | Unknown | | unknown | |
| SW13 | Adrenal | C → T | 4 | Gln 164 → STOP | P311 → S |
| C33A | Cervix | Unknown | 15 | unknown | insertion 773 Asn P316 → S |
| Panc-1 | Pancreas | Unknown | | unknown | P319→S |

To determine how the expression of these genes are altered, BRG1 and BRM mRNA transcript from each of these cell lines were sequenced. A series of nested-PCR primer pairs that yield 5 overlapping PCR products spanning the coding region of each gene were employed. These primer pairs are shown in Table 2.

TABLE 2

| | | RT-PCR Primers | |
|---|---|---|---|
| Region | exons | 5' primer | 3' primer |
| G1A | 1-3 | SEQ ID NO:1 CTGTCTGCAGCTCCCGTGAAG | SEQ ID NO:2 CGAGGGGTAACCTTGGGAGT |

TABLE 2-continued

RT-PCR Primers

| Region | exons | 5' primer | 3' primer |
|---|---|---|---|
| G1 B | 3-7 | SEQ ID NO:3<br>GGACCAGCACTCCCAAGGTT | SEQ ID NO:4<br>GCTCCTGCTCGATCTTCTGC |
| G1B-nest | | SEQ ID NO:5<br>GGACCAGCAGTCCCAAGGTT | SEQ ID NO:6<br>GCGCTTGTAGGGCTTAGCAT |
| G2 | 6-15 | SEQ ID NO:7<br>GCGAACCAAAGCGACCATTGAG | SEQ ID NO:8<br>GACAAAGGCCCGTCTTGCTG |
| G3 | 16-24 | SEQ ID NO:9<br>CATCATCGTGCCTCTCTCAAC | SEQ ID NO:10<br>ACACGCACCTCGTTCTGCTG |
| G4 | 25-34 | SEQ ID NO:11<br>AACCTCCAGTCGGCAGACAC | SEQ ID NO:12<br>ACTGGAATGTGGGGCTCAG |
| M1A | 1-4 | SEQ ID NO:13<br>TAGATGTCCACGCCCACAG | SEQ ID NO:14<br>ATGCAGCTGGACAGGACTGA |
| M1B | 5 | SEQ ID NO:15<br>CCAACTCCACCTCAGATGCC | SEQ ID NO:16<br>CTGATGCGGCTCTGCTTCT |
| M2A | 4-11 | SEQ ID NO:17<br>GGATCAACACAGCCAAGGTT | SEQ ID NO:18<br>GCCACTGCTTTGGAGAGCTT |
| M2A-nest | | SEQ ID NO:19<br>CAACAACAGCAGCAGCAACA | SEQ ID NO:20<br>GGGCCAGATGGTCTGTTGTAG |
| M2B | 10-12 | SEQ ID NO:21<br>CCTGGAGACGGCTCTCAACT | SEQ ID NO:22<br>CGTCCAGCTGACTTGCTTTG |
| M3 | 11-20 | SEQ ID NO:23<br>CTCACACAGAAACCGGCAAG | SEQ ID NO:24<br>GGCTTGCATATGGCGATACA |
| M3-nest | | SEQ ID NO:25<br>AAACCGGCAAGGTTCTGTTG | SEQ ID NO:26<br>CAGAATCTTCTGCAGAGCTGACAT |
| M4 | 19-27 | SEQ ID NO:27<br>TTGCCATGACTGGTGAAAGG | SEQ ID NO:28<br>TGAGGGCGTCACTGTAGTCC |
| M4-nest | | SEQ ID NO:29<br>GTGGAATATGTGATCAAGTGTG | SEQ ID NO:30<br>AAAGGAAGTTCCGAAAAGCAAAA |
| M5 | 27-UTR | SEQ ID NO:31<br>TTTATGCGGATGGACATGGA | SEQ ID NO:32<br>CTCATCATCCGTCCCACTTC |
| M5-nest | | SEQ ID NO:33<br>AAACGGAAGCCCCGTTTAAT | SEQ ID NO:34<br>GTCATCATCCGTCCCACTTC |

Using this approach, it was determined that five of the cell lines (SW13, H522, H513, H125 and A427) harbored mutations that could account for the loss of BRG1 expression. Three cells lines were found to contain nonsense mutations. In the SW13 cell line, a C-T transversion was found at Gln164 that created a stop codon in exon 4. In the H513 and H125 cell lines, a nonsense mutation was identified at Glu1056 in exon 21, which is just proximal to the catalytic helicase domain. It was also determined that the H522 cell line contained a 2 bp deletion at Pro269 within exon 5. Each mutation was confirmed by sequencing of the corresponding exons. Because each alteration is located upstream of the BRG1's catalytic helicase domain, the resulting proteins, if translated, would be devoid of function. As previously reported (Wong et al., Cancer Res. 60:6171-6177, 2000), it was also found that the A427 cell line contains a C-terminus truncation of the BRG1 gene. By PCR screening of each of the exons in this region, the exact location of this truncation was mapped to exons 22-35. This region includes the catalytic helicase domain, the Rb binding domain, and the bromo domain (FIG. 1A).

Several non-frameshifting indels (base pair insertions or deletions) were found within the BRG1 gene (FIG. 1A). For example, a three-base insertion that added an extra asparagine residue at amino acid 773 located in the catalytic helicase domain in the C33A cell line, as well as a Ser 1477 deletion near the C-terminus in the H23 cell line. It was found that the C33A, Panc-1, H1299, and SW13 cell lines each have a proline-to-serine missense mutation within the N-terminus of BRG1. Collectively, these point mutations cluster within in a 20-amino-acid region, GRPSPAPPAVPPAASPVMPP (SEQ ID NO:41), which is highly conserved among the human BRG1, the human BRM, and the orthologues of lower species (FIG. 1B). These mutations are located within the proline-rich region site that is similar to SH3 (Src homology 3) recognition domains, indicating they impact BRG1 interactions with other proteins.

Figure 2:
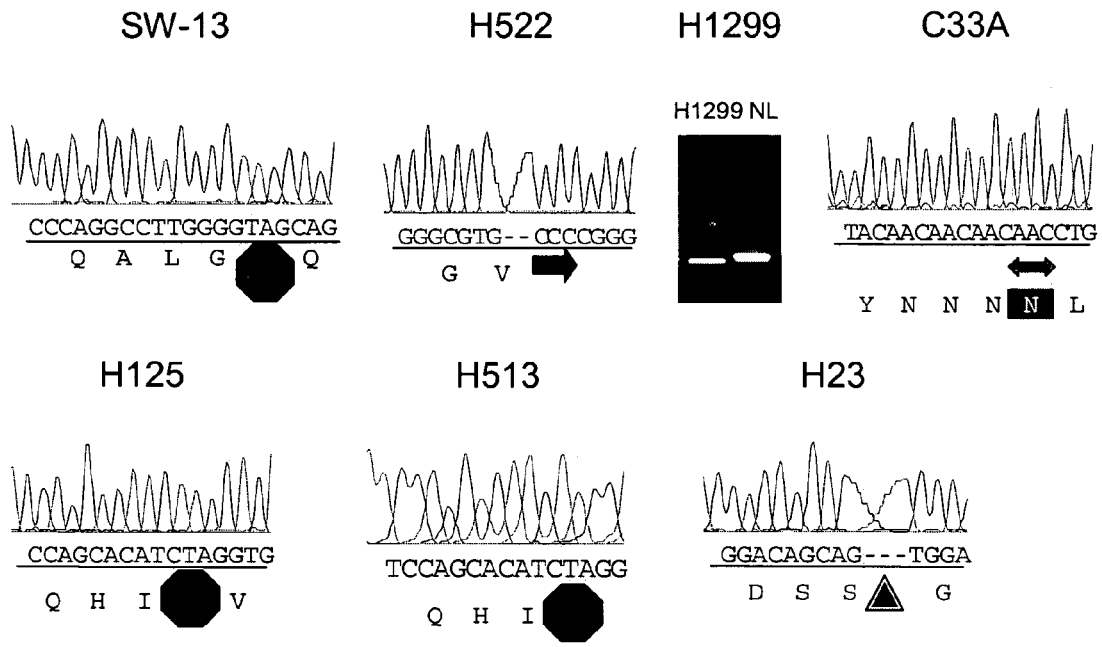
FIG. 2 shows BRG1 splicing defects in BRG1/BRM-deficient cell lines.
Figure 2:
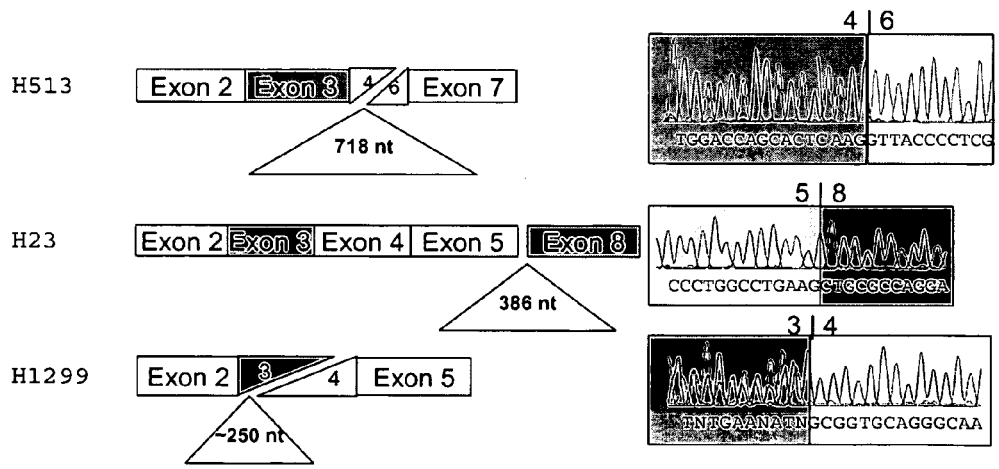

In addition to the BRG1 mutations in these cell lines, three cell lines that contained abnormal BRG1 splice variants were also uncovered. In the H1299 cell line, which has a nondisrupting in-frame 69 bp deletion of exon 10 (FIG. 2A), a 250 bp splice variant was identified in BRG1 resulting from the splicing out of most of exons 3 and 4, causing a frame-shift mutation (FIG. 2B). Aberrant splice variants in the H23 and H513 cell lines were also found (FIG. 2B). In the H23 cell line, a splicing change was detected that deleted a 386 bp region, effectively eliminating exons 6 and 7. The H513 cell line had a similar splice variant, which deletes a 718 bp region extending from exon 4 to exon 6. In each of these cases, these variant transcripts disrupted the normal reading frame. As these cell lines lack any appreciable amount of the normal transcript, the changes likely abrogate the expression of this gene.

For BRG1, a variety of mutations were found that could account for the loss of expression in 7 out of the 10 cell lines, with only the Panc-1, C33a and H1573 lacking discernable abrogating mutations. In contrast, none of the ten cell lines demonstrated any significant alterations in BRM that could account for loss of expression. Specifically, nonsense mutations, insertions, deletions, or splicing variants were not detected. This finding was confirmed by sequencing the 35 exons within the BRM gene. Thus, the mechanisms that inhibit expression of BRM and BRG1 in cancer cell lines appear to be distinctly different.

EXAMPLE 2

HDAC Inhibitors Up-Regulate the Expression of BRM But Not BRG1

This example describes the treatment of cells lines with undetectable BRG1 and BRM protein expression with various HDAC inhibitors or 5-aza-deoxycytidine (5-azaCdR). In particular, cell lines SW13, H522, H23 and A427, which have undetectable levels of BRG1/BRM proteins, were treated with DNA 5-aza-cytocytidine and sodium butyrate. 5uM 5azaCytD was applied on three consecutive days, and then examined by semi-quantative RT-PCR the expression of p16 in cell lines. Consistent with previous published reports, the silencing of p16 in H23 and H441 cell lines were reversed with this treatment. Though p16 was induced in the control cell lines, no change was detected in either the BRM or BRG1 mRNA level using semi-quantitative RT-PCR, nor was any significant increase detected in protein levels of these proteins by western blotting. These cells lines were also treated with 3 mM sodium butyrate for 3 days, and found both BRM mRNA and protein were up-regulated. In contrast, no change was found in either the BRG1 mRNA or protein levels. This upregulation effect was also examined in the six other BRG1/BRM-deficient cell lines, using RT-PCR. Of these ten cell lines, eight showed BRM transcript re-expression after butyrate treatment; only Panc-1 and H513 cell lines failed to demonstrate an appreciable induction of BRM. To assess the degree of this induction, cyber-green quantitation PCR was employed, finding that upregulation of BRM ranged from 8-20 fold in these cell lines.

To determine if the induction of BRM gene was an effect of butyrate alone, or whether it could be moderated by other known HDAC inhibitors, cell lines H522, SW13, A427, and H23 cell lines were treated with, trichostatin A, MS-275, or CI-994. Treatment with 10 μM or 100 μM of MS-275 did not greatly affect BRM expression, but at a concentration of >1 mM, a modest induction of BRM was observed that was most robust in the A427cell line. This lack of a strong induction effect, as compared to that of butyrate, is in part due to the increased toxicity of MS-275, which was most pronounced in the H23 and SW13 cell lines. Treatment with either 600 nM of trichostatin or with 5 uM of HDAC inhibitor CI-994 was also effective in inducing BRM expression in each of these cell lines.

EXAMPLE 3

Measuring BRM Expression After HDAC Inhibitor Treatment

To further investigate BRM regulation, the BRM promoter was cloned and its activity measured in BRG1/BRM positive and negative cell lines. In particular, the location of the BRM promoter was assessed by reviewing the location of available ESTs and capped cDNAs. This data showed that the BRM gene contains two first exons that are in tandem and upstream of exon2 where the translation start is located. To determine the relative usage of these alternate first exon, a screen for their expression of RT-PCR was performed. Using plasmids containing BRM1A or BRM1B cDNAs as standards, one was able to detect BRM1A mRNA but not BRM1B mRNA by RT-PCR. This was not due to a PCR conditions as the BRM1A and BRM1B cDNA equally amplified, even at low concentrations where their signals were barely detectible. Also, the vast majority of ESTs mapped to Exon1A versus Exon1B supports the role of 1A exon as the major transcription start site. To confirm transcription start site in exon1A, RACE was performed using to two different 5' primer strategies. Using mRNA from several different cell lines and normal tissues, only the BRM1A transcript was detected. Based on result on the normal tissue expression, the full length capped single cDNA spleen and thymus libraries (clontech) were obtained. By PCR, we readily detected from BRM1A and only faintly from BRM1B. These data indicate the Exon 1A is primary site transcription initiation in normal tissue and cancer cell lines.

Next, both a 741 bp and a 2.4 kd DNA fragment was closed just upstream of exon 1A into the pGL3 luficerase reporter vector. Transfecting these DNA fragment in both orientation in Calu3 and A549 yielded only robust luficerase activity when the promoters where in the correct orientation. Minimal luficerase activity was also noted with the control pGL3 in these cell lines. To determine if loss BRM expression was due to alteration in the promoter, the BRM promoter was sequenced in the 10 BRG1/BRM deficient cell lines. The several cell lines show a short insert which did appreciably altered luficerase activity when tested in Calu-6 or A549 BRM positive cell lines.

Though butyrate will promote histone acetylation by inhibiting the activity of a variety of HDACs, it is also know to promote the acetylation of varies other protein including p53 as well. To help distinguish between epigenetic chromosome condensation of the BRM promoter versus changes transcription factor activity mediate by histone acetylation, we compared activity of our BRM promoter in BRM deficient and positive cell lines. In cell lines, robust luficerase expression was found comparable to the control pGL3 vector indicating there is not dimunition of the needed transcription factor for BRM expression. We also compared the pGL3-BRM luciferase activity in the both BRM deficient with and without butyrate treated. In A427, H23, H522 and SW13 cell lines, no demonstable difference in BRM promoter activity was observed as function of butyrate treatment. Cell lines were also treated with Trichostatin and no difference in BRM promoter activity was detected.

As detailed above, in the dual luciferase assay system, no significant change was detected in relative transcriptional activity after treatment with HDAC inhibitors. These results show that BRG1 and BRM expressions are lost by different mechanisms. BRM mRNA is suppressed by epigenetic mechanisms and blocking HDAC activity restores BRM protein expression.

EXAMPLE 4

Temporal Effects of HDAC Inhibitors on BRM Re-Expression

Figure 3:
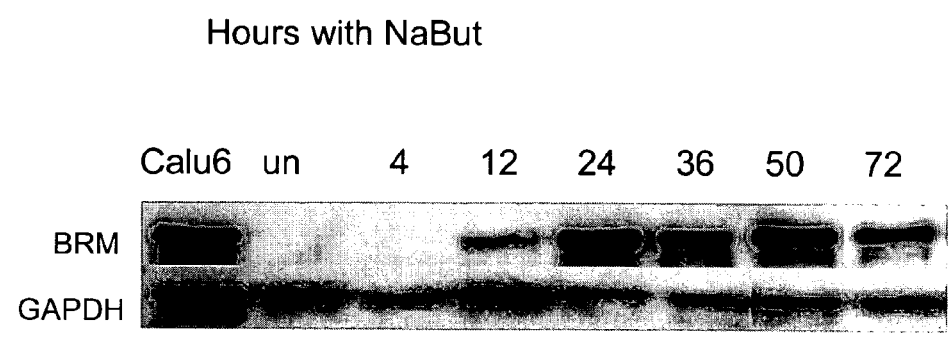
FIG. 3 shows the temporal effects of the small molecular inhibitor sodium butyrate on BRM expression.
Figure 3:
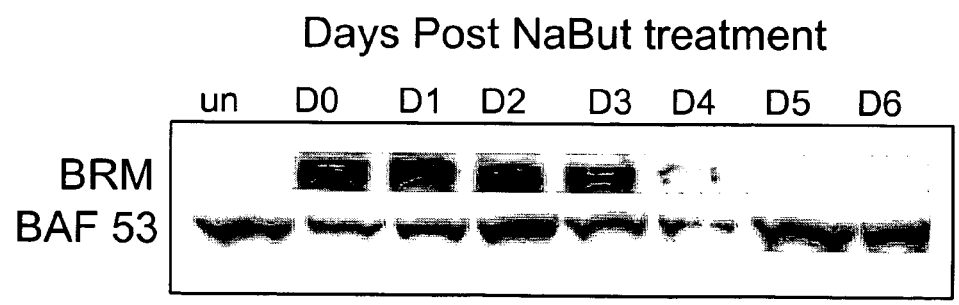

This Example describes an analysis of the temporal effects of HDAC inhibitors on BRM re-expression. In partciular, to understand how HDAC inhibitors affected BRM expression, the time course at which BRM expression in SW13 cells was induced by continued exposure to butyrate was determined. The upregulation of BRM expression was detected by western blot analysis at 12 hours and reached a plateau at 24 hours. Little change in BRM expression occurred with continued treatment for an additional 48 hours (FIG. 3A). This process was reversible, as BRM expression returned to pretreatment levels after removal of sodium butyrate. To further characterize this effect, SW13 cells were treated with butyrate for 72 hours, sodium butyrate was removed, and BRM levels were measured by western blotting from 0 to 6 days. The BRM protein levels remained elevated for 72 hours and returned to near baseline levels at 96 hours (FIG. 3B). In parallel with BRM protein, the BRM mRNA level determined by quantative RT-PCR, also remained elevated for 3 days, returning to baseline level by 4 days. These findings indicate the changes in BRM protein levels paralleled the changes in the BRM mRNA levels.

EXAMPLE 5

BRM Expression is Lost in a Variety of Human Cancer

The Example describes a determination of which of the various common solid tumor types demonstrate the BRM deficiency. To accomplish this, six different high-density, tissue-specific microarrays were immunostained: lung, esophageal, ovarian, bladder, colon, and breast carcinomas, using a BRM-specific polyclonal antibody.

Anti-BRM antigen was prepared from the expression plasmid, pGEX-GST-BRM, containing a cDNA fragment of mouse BRM gene (encoding amino acid residues 50-214 in the corresponding human sequence) in pGEX-5X-2. The GST-BRM fusion protein was expressed in *E. coli* BL21 and purified on a glutathione-Sepharose 4B column (Amersham, Piscataway, N.J.) and GST-BRM fusion protein was used to produce rabbit polyclonal antibodies (Rockland, Rockland, Md.). The resulting BRM antisera was then passed over a GST-BRG1 column to remove GST or BRG1 reacting antibodies, and this negatively purified antisera was then further immunopurified by passing it over GST-BRM column. BRM specificity and lack of BRG1 cross reactivity of double affinity immunopurified antisera were confirmed by immunostaining paraffin embedded BRG1/BRM-deficient cell lines SW13 and H522 transfected with either BRG1 or BRM.

The lung TMA was derived from surgery resection of pathological stage 1 and 2 cases at the University of Michigan from 1997-2001. Similarly breast, colon, esophageal, bladder, and ovarian TMAs were constructed from University of Michigan surgical cases and were gifts from Drs. Kleer, Giordano, Beer, Shah and Cho, respectively.

In preparation for immunostaining, TMA sections were deparaffinized with xylene and hydrated in a descending ethanol series to ddH2O. Before proceeding to antigen retrieval, sections were incubated 5 min in 1× PBS. Sections were immersed in 250 ml of 10 mM Tris-buffer, pH 10.0 in a covered plastic histology tank and placed in a microwaveable pressure cooker (Nordic Ware, Minneapolis, Minn.) containing 200 ml ddH2O. Sections were microwaved for 15 min at maximum power, then allowed to cool in the closed microwave for 10 min. After removal from the microwave, sections were slowly cooled in the sealed pressure cooker for 10 minutes under cold running water. Upon removal from the pressure cooker, sections were washed 5 min under cool ddH2O and transferred to 1× PBS for 5 minutes. To eliminate endogenous peroxidase activity, slides were immersed in 3% H2O2 for 15 min and washed with 1× PBS. Sections were blocked 10 minutes in 3% PBSA then incubated 60 min at room temperature with a 1:5000 dilution of anti-rabbit-GST-BRM, rinsed with 1× PBS, and incubated 30 minutes with a 1:150 dilution of the biotinylated goat-a-rabbit secondary antibody (BD Biosciences, San Diego, Calif.). After a wash with 1× PBS, sections were incubated with horseradish peroxidase-conjugated streptavidin (BD Biosciences) 30 minutes at room temperature. Sections were rinsed with 1× PBS and chromogen developed for 5-10 min with diaminobenzidine (DAB) solution. Finally, sections were counterstained with Harris Hematoxlyin (Fisher, Middletown, Va.), dehydrated, and mounted with Permount (Fisher).

All cases were reviewed by the pathologists in the study. Intensity of staining was defined as negative (no staining), weak (low staining), and positive (moderate and strong intensity) in over 80% of the tumor cells. All TMAs were reviewed blindly to clinical and pathological information.

As with previously reported results in lung cancer (Reisman et al., Oncogene, 21:1196-1207, 2002), it was found that for each tumor type examined, ~15% cases had negative BRM protein expression, and that ~1-2% had weak BRM expression (Table 3). Table 3 summarizes the expression of BRM protein on different types of human carcinomas studied.

TABLE 3

Frequency of BRM Loss in Different Cancer Types

| Tumor Type | Number | % Negative | % Weak | % Positive |
|---|---|---|---|---|
| Bladder | | | | |
| Transitional Cell | 66.0 | 15.2 | 3.0 | 81.8 |
| Esophagus | 112.0 | 8.6 | 3.7 | 91.1 |
| Barrett's | 31.0 | 0.0 | 0.0 | 100.0 |
| Adenocarinoma | 81.0 | 8.6 | 3.7 | 87.7 |
| Ovary | 62.0 | 17.7 | 4.8 | 74.2 |
| Clear Cell | 11.0 | 27.3 | 9.0 | 63.7 |
| Mucinous | 10.0 | 10.0 | 0.0 | 90.0 |
| Endometrioid | 17.0 | 17.6 | 5.9 | 76.5 |
| Serous | 22.0 | 18.2 | 4.5 | 77.3 |
| Breast | 168.0 | 14.9 | 13.1 | 72.0 |
| Ductal | 151 | 15.2 | 13.4 | 73.7 |
| Lobular | 17 | 17.6 | 11.8 | 56.9 |
| Lung Cancer | 160.0 | 15.8 | 1.7 | 82.5 |
| Squamous Cell | 44.0 | 15.2 | 3.0 | 81.8 |
| Adenocarcinoma | 97.0 | 16.4 | 1.4 | 82.2 |
| Large Cell | 8.0 | 16.7 | 0.0 | 83.3 |
| Other | 11.0 | 12.5 | 0.0 | 87.5 |

Although BRM has roles in both development and differentiation, in both lung an ovarian carcinomas, the loss BRM occurred with similar frequencies in the different histology subtypes (Table 3).

Other analysis did not find an association between BRM expression and the histological grade, a measure of tumor differentiation in non-small cell lung. Using 30 BRM negative cases and 170 BRM positive nonsmall cell lung cancer cases, the correlation between their differentiation states (poor, moderate and well) was examined by computing the independence test for each state of the two variables. The results showed a statistically insignificant result at the 5% level. From these data, it appears that the distribution of BRM-negative and -positive tumors is independent of differentiation state. Moreover, BRM expression was reduced in approximately 10% of esophageal cancers, but was retained in 31 Barrett's lesions examined, a precursor lesion for esophageal carcinoma, suggesting that BRM loss may not occur early in cancer development, but may be a hallmark of neoplastic transformation.

EXAMPLE 6

Loss of BRM Expression Can Potentiate Tumor Developmnet

This Example describes methods used to test the role of BRM loss as it contributes to cancer progression. An established experimental approach was employed that has previously been used to support the tumorigenic roles of such genes as Krev-1, p21, RASSFA1 and Testin (see, e.g., Drusco et al., PNAS USA 102:10947-10951, 2005, and Tommasi et al., Cancer Res. 65:92-98, 2005). In this model, transgenic mice are exposed to a known carcinogen and the differential effects on tumor occurrence are then studied. Using this approach, we treated mice lacking one or both BRM alleles with the lung-specific carcinogen urethane and determined if there was an increase in the number of lung tumors compared to wild type BRM control mice.

Figure 4:
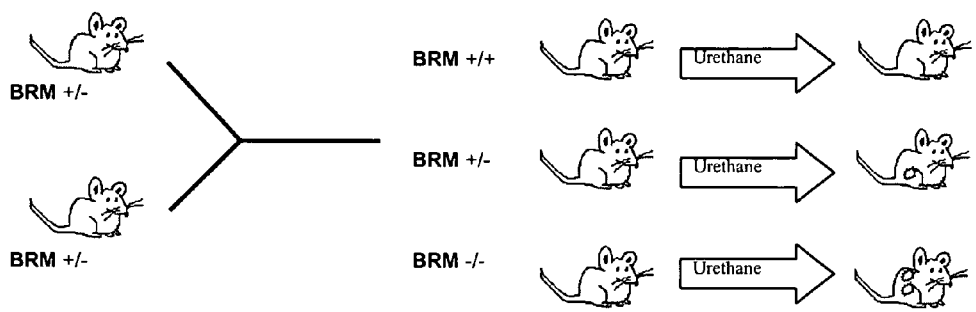
FIG. 4A shows the experimental design of the mouse breeding and sequential treatment with the lung-specific carcinogen, urethane, described in Example 6.
FIG. 4B shows that the number of tumors in the mice 12 weeks post urethane treatment for mice that were wild type, heterozygous or null for BRM expression. Compared to wild type mice, BRM heterozygous and BRM null had approximately 4- and 10-fold more tumors on the surface of the lung, respectively.
FIG. 4C shows that when tumors were counted in cross sections, a 3- and 7-fold increase in tumors was found when one or both BRM alleles were missing.
Figure 4:
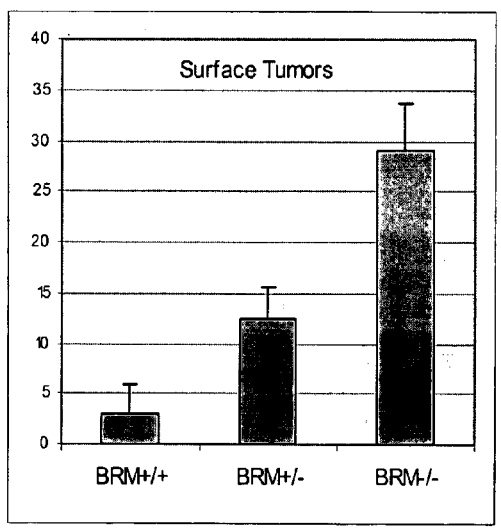
Figure 4:
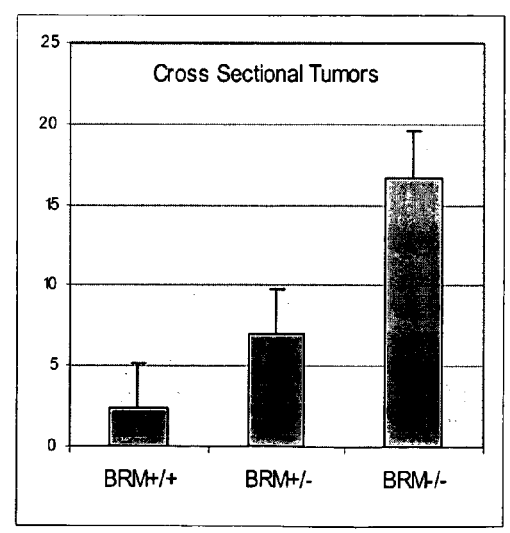

To accomplish this, we cross-bred heterozygous BRM mice to generate wild type, heterozygous, or null BRM mice (FIG. 4A). The BRM null mice were a gift from Moshe Yaniv, and their generation has been previously described (Miller et al., Cancer Lett, 198:139-144, 2003). The BRM null mice are of 129/SV background and were crossed with 129/SV mice to BRM heterozygous mice. Mice were treated at 8 weeks of age with intraperitoneal urethane 1 mg/kg and then monitored for tumor development in the lungs by sacrificing two mice from each group every 4 weeks. At 20 weeks, tumor development was observed in the control mice (BRM wild type mice). At this juncture, the balance of the mice in each group (n=10 per group) were sacrificed and the effect of BRM expression on tumor development were compared by counting the number of visible surface tumors. It was found that a sequential increase in the number of tumors developing was a function of BRM allelic loss. Specifically, BRM wild-type mice had 2-3 tumors per mouse, whereas BRM heterozygous and BRM null mice had 12 and 25 tumors per mouse, respectively (FIG. 4B panel B). Similarly increased numbers were observed when cross-sections of the lungs of these animals were examined (FIG. 4C). However, a significant difference in tumor size or difference in histology type between these groups was not observed. Although loss of BRM and BRG1 frequently occurs together, this increase in tumorigenicity was not attributable to concomitant loss of BRG1, because staining these mice for BRG1 showed that BRG1 expression was retained.

Thus, loss of BRM can potentiate tumor development when combined with other molecular changes or exposure to carcinogens.

EXAMPLE 7

Genes Up-Regulated Upon Reexpression of BRM

This Example describes methods used to analyze genes that are up-regulated upon reexpression of BRM. In particular, microarray analysis was used to determine the identity of genes that were up-regulated at least four-fold or more when BRM negative cell lines either SW13, A427 or NCI-H522 were transiently transfected with BRM (pCG-BRM vector) and a GFP expression vector and then were sorted by flow cytometry to selected for positively transfected subpopulation. As control, the same cell lines were transfect with GFP alone and also sorted by flowcytometry. Table 4 presents the list of genes found to be up-regulated four-fold or more in at least 2 of the 3 three cell examined. The genes are broken down into seven categories: i) differentiation genes; ii) tumor suppressor/oncogene/DNA repair genes; iii) cell adhesion genes; iv) extracellular matrix/structural genes; v) chemokine genes; vi) interferon-inducible genes; and vii) other genes.

TABLE 4

| | |
|---|---|
| Differentiation | |
| LBH | likely ortholog of mouse limb-bud and heart gene |
| Tumor suppressor/Oncogene/DNA Repair | |
| GADD45A | growth arrest and DNA-damage-inducible, alpha |
| LCN2 | lipocalin 2 (oncogene 24p3) |
| RARRES3 | retinoic acid receptor responder (tazarotene induced) 3 |
| KLF4 | Kruppel-like factor 4 (gut) |
| S100A2 | S100 calcium binding protein A2 |
| BCAR3 | breast cancer anti-estrogen resistance 3 |
| Cell Adhesion | |
| SPARC | secreted protein, acidic, cysteine-rich (osteonectin) |
| CEACAM1 | carcinoembryonic antigen-related cell adhesion molecule 1 (biliary glycoprotein) |
| CD44 | CD44 antigen (homing function and Indian blood group system) |
| CDH1 | cadherin 1, type 1, E-cadherin (epithelial) |
| SPARCL1 | SPARC-like 1 (mast9, hevin) |
| Extracellular Matrix/Structural | |
| PODXL | podocalyxin-like |
| LGALS3BP | lectin, galactoside-binding, soluble, 3 binding protein |
| MMP1 | matrix metalloproteinase 1 (interstitial collagenase) |
| SERPINE1 | serine (or cysteine) proteinase inhibitor, clade E (nexin, plasminogen activator inhibitor type 1), member 1 |
| CRYAB | crystallin, alpha B |
| BST2 | bone marrow stromal cell antigen 2 |
| MFAP5 | microfibrillar associated protein 5 |
| PLAU | plasminogen activator, urokinase |
| PI3 | protease inhibitor 3, skin-derived (SKALP) |
| PRSS23 | protease, serine, 23 |
| CHI3L1 | chitinase 3-like 1 (cartilage glycoprotein-39) |
| MFAP5 | microfibrillar associated protein 5 |
| KRT18 | keratin 18 |
| LAMB | laminin, beta |
| CEACAM1 | carcinoembryonic antigen-related cell adhesion molecule 1 (biliary glycoprotein) |
| TAGLN | transgelin |
| SLPI | secretory leukocyte protease inhibitor (antileukoproteinase) |

TABLE 4-continued

| | |
|---|---|
| SERPINB9 | serine (or cysteine) proteinase inhibitor, clade B (ovalbumin), member 9 |
| P8 | p8 protein (candidate of metastasis 1) |
| CHI3L1 | chitinase 3-like 1 (cartilage glycoprotein-39) |
| TIMP3 | tissue inhibitor of metalloproteinase 3 (Sorsby fundus dystrophy, pseudoinflammatory) |
| MATN2 | matrilin 2 |
| PLAT | plasminogen activator, tissue |
| SVIL | supervillin |
| ITGA3 | integrin, alpha 3 (antigen CD49C, alpha 3 subunit of VLA-3 receptor) |
| Chemokines | |
| CCL5 | chemokine (C—C motif) ligand 5 |
| CXCL11 | chemokine (C—X—C motif) ligand 11 |
| CXCL10 | chemokine (C—X—C motif) ligand 10 |
| CXCR4 | chemokine (C—X—C motif) receptor 4 |
| CXCL11 | chemokine (C—X—C motif) ligand 11 |
| CCL5 | chemokine (C—C motif) ligand 5 |
| CCL2 | chemokine (C—C motif) ligand 2 |
| Interferon-inducible | |
| IFIT3 | interferon-induced protein with tetratricopeptide repeats 3 |
| IFIT2 | interferon-induced protein with tetratricopeptide repeats 2 |
| IFITM1 | interferon induced transmembrane protein 1 (9–27) |
| IFI27 | interferon, alpha-inducible protein |
| IFIT3 | interferon-induced protein with tetratricopeptide repeats 3 |
| OASL | 2'-5'-oligoadenylate synthetase-like |
| IFITM1 | interferon induced transmembrane protein 1 (9–27) |
| OAS2 | 2'-5'-oligoadenylate synthetase 2, 69/71 kDa |
| OAS1 | 2',5'-oligoadenylate synthetase 1, 40/46 kDa |
| IFI44 | interferon-induced protein 44 |
| IFITM3 | interferon induced transmembrane protein 3 (1–8U) |
| IFITM2 | interferon induced transmembrane protein 2 (1–8D) |
| TGM2 | transglutaminase 2 (C polypeptide, protein-glutamine-gamma-glutamyltransferase) |
| IFIH1 | interferon induced with helicase C domain 1 |
| ISG20 | interferon stimulated gene 20 kDa |
| IFI16 | interferon, gamma-inducible protein 16 |
| OAS3 | 2'-5'-oligoadenylate synthetase 3, 100 kDa |
| IFIT5 | interferon-induced protein with tetratricopeptide repeats 5 |
| IFI16 | interferon, gamma-inducible protein 16 |
| G1P3 | interferon, alpha-inducible protein (clone IFI-6-16) |
| ISG20 | interferon stimulated gene 20 kDa |
| IFI44L | interferon-induced protein 44-like |
| LOC391020 | similar to Interferon-induced transmembrane protein 3 (Interferon-inducible protein 1–8U) |
| GBP1 | guanylate binding protein 1, interferon-inducible, 67 kDa |
| IFIT1 | interferon-induced protein with tetratricopeptide repeats 1 |
| TIMP3 | tissue inhibitor of metalloproteinase 3 (Sorsby fundus dystrophy, pseudoinflammatory) |
| ISGF3G | interferon-stimulated transcription factor 3, gamma 48 kDa |
| IFIT5 | interferon-induced protein with tetratricopeptide repeats 5 |
| IFIH1 | interferon induced with helicase C domain 1 |
| G1P2 | interferon, alpha-inducible protein (clone IFI-15K) |
| Other | |
| PARG1 | PTPL1-associated RhoGAP 1 |
| F2RL1 | coagulation factor II (thrombin) receptor-like 1 |
| RSAD2 | radical S-adenosyl methionine domain containing 2 |
| TRIM22 | tripartite motif-containing 22 |
| RSAD2 | radical S-adenosyl methionine domain containing 2 |
| LOC129607 | hypothetical protein LOC129607 |
| HERC5 | hect domain and RLD 5 |
| FER1L3 | fer-1-like 3, myoferlin (C. elegans) |
| SAMD9 | sterile alpha motif domain containing 9 |
| DDX58 | DEAD (Asp-Glu-Ala-Asp) box polypeptide 58 |
| TNFSF10 | tumor necrosis factor (ligand) superfamily, member 10 |

TABLE 4-continued

| | |
|---|---|
| IGFBP6 | insulin-like growth factor binding protein 6 |
| GBP3 | guanylate binding protein 3 |
| PIK3AP1 | phosphoinositide-3-kinase adaptor protein 1 |
| FER1L3 | fer-1-like 3, myoferlin (C. elegans) |
| SMARCA2 | SWI/SNF related, matrix associated, actin dependent regulator of chromatin, subfamily a, member 2 |
| COLEC12 | collectin sub-family member 12 |
| PMAIP1 | phorbol-12-myristate-13-acetate-induced protein 1 |
| NCF2 | neutrophil cytosolic factor 2 (65 kDa, chronic granulomatous disease, autosomal 2) |
| HERC6 | hect domain and RLD 6 |
| S100A16 | S100 calcium binding protein A16 |
| SP100 | Nuclear antigen Sp100 |
| PDLIM1 | PDZ and LIM domain 1 (elfin) |
| ATP8B1 | ATPase, Class I, type 8B, member 1 |
| HSXIAPAF1 | XIAP associated factor-1 |
| ATF3 | activating transcription factor 3 |
| PPM2C | protein phosphatase 2C, magnesium-dependent, catalytic subunit |
| FLJ20035 | hypothetical protein FLJ20035 |
| GPCR5A | G protein-coupled receptor, family C, group 5, member A |
| MFAP5 | microfibrillar associated protein 5 |
| STK17A | serine/threonine kinase 17a (apoptosis-inducing) |
| GPNMB | glycoprotein (transmembrane) nmb |
| PPM2C | protein phosphatase 2C, magnesium-dependent, catalytic subunit |
| ZC3HAV1 | zinc finger CCCH type, antiviral 1 |
| DDX58 | DEAD (Asp-Glu-Ala-Asp) box polypeptide 58 |
| PMAIP1 | phorbol-12-myristate-13-acetate-induced protein 1 |
| TNFSF10 | tumor necrosis factor (ligand) superfamily, member 10 |
| GPNMB | glycoprotein (transmembrane) nmb |
| DTX3L | deltex 3-like (Drosophila) |
| DUSP5 | dual specificity phosphatase 5 |
| CDNA clone | IMAGE: 6025865, partial cds |
| SAMD9 | sterile alpha motif domain containing 9 |
| PI3 | protease inhibitor 3, skin-derived (SKALP) |
| PARP9 | poly (ADP-ribose) polymerase family, member 9 |
| PARP14 | poly (ADP-ribose) polymerase family, member 14 |
| MX2 | myxovirus (influenza virus) resistance 2 (mouse) nuclear antigen Sp100SP100 |
| NT5E | 5'-nucleotidase, ecto (CD73) |
| PLSCR1 | phospholipid scramblase 1 |
| UBD | ubiquitin D |
| MICAL2 | flavoprotein oxidoreductase |
| SAT | Spermidine/spermine N1-acetyltransferase |
| NMI | N-myc (and STAT) interactor |
| C20orf100 | chromosome 20 open reading frame 100 |
| PPP1R6B | protein phosphatase 1, regulatory (inhibitor) subunit 16B |
| LRIG1 | leucine-rich repeats and immunoglobulin-like domains 1 |
| LAMP3 | lysosomal-associated membrane protein 3 |
| FHL1 | four and a half LIM domains 1 |
| PLSCR1 | phospholipid scramblase 1 |
| GPR56 | G protein-coupled receptor 56 |
| F2R | coagulation factor II (thrombin) receptor |
| FAM43A | family with sequence similarity 43, member A |
| C1orf17.SNARK | chromosome 11 open reading frame 17/likely ortholog of rat SNF1/AMP-activated protein kinase |
| HBEGF | heparin-binding EGF-like growth factor |
| DKK3 | dickkopf homolog 3 (Xenopus laevis) |
| FLJ22761 | hypothetical protein FLJ22761 |
| STK17A | serine/threonine kinase 17a (apoptosis-inducing) |
| CA12 | carbonic anhydrase XII |
| UBE2L6 | ubiquitin-conjugating enzyme E2L 6 |
| C7orf6 | chromosome 7 open reading frame 6 |
| CPA4 | carboxypeptidase A4 |

EXAMPLE 8

BRM Promoter Polymorphisms

This Example describes the discovery of polymorphism in the human BRM promoter. In particular, the presence of two polymorphisms within the BRM promoter have been discovered. Each polymorphism is a 7 or 6 base pair insertion located at base pairs 741 and 1321 respectively. The sequence of the 7 base pair insertion at position 741 was determined to be TATTTTT (SEQ ID NO:53), and the 6 base pair insertion at position 1321 was determined to be TTTTAA (SEQ ID NO:43). Importantly, the polymorphism at 741 strongly correlates with the loss of BRM expression while the 1321 does not. FIG. 5 shows the human BRM promoter with position 741 highlighted.

To determine if there was a specific association between BRM loss and this polymorphism, the BRM promoter from about 40 normal randomly-chosen individuals was sequenced. The results are shown in Table 5 below.

TABLE 5

Data Collected

|  | Wild (bb) | Hetero (Bb) | Homo/Insert (BB) | Tot. |
|---|---|---|---|---|
| Control | 16 | 11 | 5 | 32 |
| BRM neg | 4 | 0 | 8 | 12 |
| BRM pos | 2 | 1 | 4 | 7 |
| Control | 9 | 16 | 6 | 31 |
| BRM neg | 5 | 1 | 6 | 12 |
| BRM pos | 4 | 3 | 1 | 8 |

Allele Frequency

|  |  | 95% Confidence Interval | |
|---|---|---|---|
|  | Est. | Lower Bound | Upper Bound |
| Control | 0.33 | 0.21 | 0.45 |
| BRM neg | 0.67 | 0.47 | 0.86 |
| BRM pos | 0.64 | 0.39 | 0.90 |
| Control | 0.45 | 0.33 | 0.58 |
| BRM neg | 0.54 | 0.34 | 0.75 |
| BRM pos | 0.31 | 0.08 | 0.54 |

Risk Ratio Relative to Controls

|  |  | 95% Confidence Interval | |
|---|---|---|---|
|  | Est. | Lower Bound | Upper Bound |
| BRM neg | 2.03 | 1.10 | 2.97 |
| BRM pos | 1.96 | 0.91 | 3.01 |

TABLE 5-continued

| BRM neg | 1.20 | 0.64 | 1.76 |
| BRM pos | 0.69 | 0.14 | 1.24 |

It was estimated that the approximate frequency of this polymorphism in the general population was about 41%, with a homozygous state occurring in 17% of people. In contrast, 71% of BRM-negative cell lines demonstrate the presence of this polymorphism. These percentages would not occur at this frequency unless 85% of individuals were positive for this polymorphism. Thus, this is statistically significant, indicating that the high frequency of this polymorphism in BRM negative cell lines is not occurring due to chance alone.

As HDAC inhibitors induce the expression of BRM in these cell lines, it is important to note that the 741 polymorphism is actually a known binding sequence for transcription factor MEF2A. MEF2A is known to recruit HDACs. While not necessary to understand to practice the present invention, it appears that people who are functionally homozygous for this polymorphic allele have a much higher chance of having BRM silenced, and this likely occurs because they have extra/additional sites in their promoter which is utilized to recruit HDAC enzymes. Also, it was noted that there were no "BRM-negative cell lines" which were heterozygous at the 741 locus. By definition, loss of heterozygosity was observed. Functionally, while not necessary to understand to practice the present invention, what appears to happen is that tumors arising from individuals which are heterozygous at 741 lose the wild type allele and thus become functionally homozygous for the BRM 741 polymorphism. Therefore, the tumors are likely silencing BRM by losing the wild type allele and then by silencing the 741 allele via the aberrant recruitment of HDACs.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

I claim:

1. A method for identifying an active BRM expression-promoting histone deacetylase inhibitor that does not inactive BRM via acetylation and that specifically inhibits HDAC3 comprising;
   a) providing;
      i) a candidate histone deacetylase inhibitor; and
      ii) at least one cell, wherein said cell exhibits reduced BRM protein or BRM mRNA expression;
   b) contacting said cell with said candidate histone deacetylase inhibitor,
   c) measuring BRM protein or BRM mRNA expression exhibited by said cell, or measuring CD44 protein or CD44 mRNA expression exhibited by said cell, wherein an increase in said BRM protein expression, BRM mRNA expression, CD44 protein expression, or CD44 mRNA expression exhibited by said cell identifies said candidate histone deacetylase inhibitor as a BRM expression-promoting histone deactylase inhibitor;
   d) identifying said candidate histone deacetylase inhibitor as a BRM expression-promoting histone deactylase inhibitor; and
   e) determining that said BRM protein expressed after said contacting is active BRM protein capable of forming a functional SWI/SNF complex, thereby indentifying said BRM expression-promoting histone deacytlase inhibitor as an active BRM expression-promoting histone deacetylase inhibitor that does not inactivate BRM via acetylation and that specifically inhibits HDAC3.

2. The method of claim 1, wherein said cell further exhibits reduced wild-type BRG1 protein or wild-type BRG1 mRNA expression.

3. The method of claim 1, wherein said cell is a cancer cell.

4. The method of claim 1, wherein said cancer cell is breast cancer cell or a prostate cancer cell.

5. The method of claim 1, wherein said determining that said BRM protein expressed after said contacting is active BRM protein capable of forming a functional SWI/SNF complex comprises detecting vimentin protein or mRNA expression.

6. The method of claim 1, wherein said determining that said BRM protein expressed after said contacting is active BRM protein capable of forming a functional SWI/SNF complex comprises detecting CD44 protein or mRNA expression.

7. The method of claim 1, wherein said determining that said BRM protein expressed after said contacting is active BRM protein capable of forming a functional SWI/SNF complex comprises detecting PPARgamma protein or mRNA expression.

8. The method of claim 1, wherein said determining that said BRM protein expressed after said contacting is active BRM protein capable of forming a functional SWI/SNF complex comprises detecting retinoblastoma protein growth inhibition.

9. The method of claim 1, wherein said determining that said BRM protein expressed after said contacting is active BRM protein capable of forming a functional SWI/SNF complex comprises detecting BRCAlprotein or mRNA expression.

10. The method of claim 1, wherein said determining that said BRM protein expressed after said contacting is active BRM protein capable of forming a functional SWI/SNF complex comprises detecting Farconi's anemia protein, protein or mRNA expression.

11. The method of claim 1, wherein said determining that said BRM protein expressed after said contacting is active BRM protein capable of forming a functional SWI/SNF complex comprises detecting Ceacam-1 protein or mRNA expression.

12. The method of claim 1, wherein said determining that said BRM protein expressed after said contacting is active BRM protein capable of forming a functional SWI/SNF complex comprises detecting Sparc protein or mRNA expression.

13. The method of claim 1, wherein said determining that said BRM protein expressed after said contacting is active BRM protein capable of forming a functional SWI/SNF complex comprises detecting LBH protein or mRNA expression.

14. The method of claim 1, wherein said determining that said BRM protein expressed after said contacting is active BRM protein capable of forming a functional SWI/SNF complex comprises detecting p53 protein or mRNA expression.

15. The method of claim 1, wherein said determining that said BRM protein expressed after said contacting is active BRM protein capable of forming a functional SWI/SNF complex comprises detecting p107 protein or mRNA expression.

* * * * *

SEQUENCE LISTING

<160> NUMBER OF SEQ ID NOS: 53

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ctgtctgcag ctcccgtgaa g                    21

```
<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2 cgagggtaa ccttgggagt                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ggaccagcac tcccaaggtt                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gctcctgctc gatcttctgc                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggaccagcac tcccaaggtt                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gcgcttgtag gccttagcat                                                   20

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gcgaaccaaa gcgaccattg ag                                                22

<210> SEQ ID NO 8
<211> LENGTH: 20
<212> TYPE: DNA
<213> ORGANISM: Artificial Sequence
<220> FEATURE:
<223> OTHER INFORMATION: Synthetic
```

-continued

```
<400> SEQUENCE: 8
gacaaaggcc cgtcttgctg                                               20

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
catcatcgtg cctctctcaa c                                             21

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
acacgcacct cgttctgctg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
aacctccagt cggcagacac                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
actggaatgt cggggctcag                                               20

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
tagatgtcca cgcccacag                                                19

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
atgcagctgg acaggactga                                               20
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccaactccac ctcagatgcc                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
ctgatgcggc tctgcttct                                               19

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ggatcaacac agccaaggtt                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gccactgctt tggagagctt                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
caacaacagc agcagcaaca                                              20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
gggccagatg gtctgttgta g                                            21

<210> SEQ ID NO 21
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 21
cctggagacg gctctcaact                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
cgtccagctg acttgctttg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ctcacacaga aaccggcaag                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
ggcttgcata tggcgataca                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
aaaccggcaa ggttctgttc                                              20

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
cagaatcttc tgcagagctg acat                                         24

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ttgccatgac tggtgaaagg                                              20
```

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tgagggcgtc actgtagtcc                                              20

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
gtggaatatg tgatcaagtg tg                                           22

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
aaaggaagtt ccgaaaagca aaa                                          23

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
tttatgcgga tggacatgga                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ctcatcatcc gtcccacttc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
aaacggaagc cccgtttaat                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic

```
<400> SEQUENCE: 34
ctcatcatcc gtcccacttc                                                  20

<210> SEQ ID NO 35
<211> LENGTH: 68
<212> TYPE: PRT
<213> ORGANISM: Artificial Sequence
<220> FEATURE:
<223> OTHER INFORMATION: Synthetic

<400> SEQUENCE: 35

Ala Asn Ala Ala Ala Pro Thr Ser Thr Pro Gln Lys Leu Ile Pro Pro
1               5                   10                  15

Gln Pro Thr Gly Arg Pro Ser Pro Ala Pro Ala Val Pro Pro Ala
            20                  25                  30

Ala Ser Pro Val Met Pro Pro Gln Thr Gln Ser Pro Gly Gln Pro Ala
        35                  40                  45

Gln Pro Ala Pro Met Val Pro Leu His Gln Lys Gln Ser Arg Ile Thr
    50                  55                  60

Pro Ile Gln Lys
65

<210> SEQ ID NO 36
<211> LENGTH: 68
<212> TYPE: PRT
<213> ORGANISM: Artificial Sequence
<220> FEATURE:
<223> OTHER INFORMATION: Synthetic

<400> SEQUENCE: 36

Ala Asn Ala Ala Ala Pro Ala Thr Ala Pro Gln Lys Leu Ile Pro Pro
1               5                   10                  15

Gln Pro Thr Gly Arg Pro Ser Pro Ala Pro Ala Val Pro Pro Ala
            20                  25                  30

Ala Ser Pro Val Met Pro Pro Gln Thr Gln Ser Pro Gly Gln Pro Ser
        35                  40                  45

Gln Pro Pro Pro Ile Val Gln Phe His Ser Lys Leu Asn Arg Ile Thr
    50                  55                  60

Pro Ile Gln Lys
65

<210> SEQ ID NO 37
<211> LENGTH: 65
<212> TYPE: PRT
<213> ORGANISM: Artificial Sequence
<220> FEATURE:
<223> OTHER INFORMATION: Synthetic

<400> SEQUENCE: 37

Asn Ala Ala Ala Pro Ala Ser Ala Pro Gln Lys Leu Ile Pro Pro Gln
1               5                   10                  15

Pro Thr Gly Arg Pro Ser Pro Ala Pro Ser Val Pro Ala Ala
            20                  25                  30

Ser Pro Val Met Pro Pro Gln Thr Gln Ser Pro Gly Gln Pro Ala Gln
        35                  40                  45

Pro Pro Met Val Leu His Gln Lys Gln Asn Arg Ile Thr Pro Ile Gln
    50                  55                  60

Lys
65
```

```
<210> SEQ ID NO 38
<211> LENGTH: 66
<212> TYPE: PRT
<213> ORGANISM: Artificial Sequence
<220> FEATURE:
<223> OTHER INFORMATION: Synthetic

<400> SEQUENCE: 38

Pro Gly Pro Glu Leu Ser Gly Pro Ser Thr Pro Gln Lys Leu Pro Val
1               5                   10                  15

Pro Ala Pro Gly Gly Arg Pro Ser Pro Ala Pro Pro Ala Ala Ala Gln
            20                  25                  30

Pro Pro Ala Ala Ala Val Pro Gly Pro Ser Val Pro Gln Pro Ala Pro
        35                  40                  45

Gly Gln Pro Ser Pro Val Leu Gln Leu Gln Gln Lys Gln Ser Arg Ile
    50                  55                  60

Ser Pro
65

<210> SEQ ID NO 39
<211> LENGTH: 65
<212> TYPE: PRT
<213> ORGANISM: Artificial Sequence
<220> FEATURE:
<223> OTHER INFORMATION: Synthetic

<400> SEQUENCE: 39

Gln Pro Gln Val Arg Gly Thr Leu Pro Gly Met Pro Pro Gly Ser Gln
1               5                   10                  15

Val Pro Gln Pro Gly Gly Gly Pro Gln Arg Gln Val Pro Pro Ala Gly
            20                  25                  30

Met Pro Met Pro Lys Pro Asn Arg Ile Thr Thr Val Ala Lys Pro Val
        35                  40                  45

Gly Leu Asp Pro Ile Thr Leu Leu Gln Glu Arg Glu Asn Arg Ile Ala
    50                  55                  60

Ala
65

<210> SEQ ID NO 40
<211> LENGTH: 37
<212> TYPE: PRT
<213> ORGANISM: Artificial Sequence
<220> FEATURE:
<223> OTHER INFORMATION: Synthetic

<400> SEQUENCE: 40

Pro Pro Ser Pro Gln Lys Leu Val Pro Gln Pro Gly Gly Arg Pro Ser
1               5                   10                  15

Pro Ala Pro Pro Ala Ala Pro Pro Gln Pro Pro Leu Gln Gln Lys
            20                  25                  30

Gln Asn Arg Ile Pro
        35

<210> SEQ ID NO 41
<211> LENGTH: 20
<212> TYPE: PRT
<213> ORGANISM: Artificial Sequence
<220> FEATURE:
<223> OTHER INFORMATION: Synthetic
```

<400> SEQUENCE: 41

Gly Arg Pro Ser Pro Ala Pro Pro Ala Val Pro Pro Ala Ala Ser Pro
1               5                   10                  15

Val Met Pro Pro
            20

<210> SEQ ID NO 42
<211> LENGTH: 952
<212> TYPE: DNA
<213> ORGANISM: Artificial Sequence
<220> FEATURE:
<223> OTHER INFORMATION: Synthetic

<400> SEQUENCE: 42

| ttagcgaaga tggcaggtga gggaaggtta tagtgctgta cctagtccac gaagtaaaca | 60 |
| gagaggttag ggtgggttta cttatttata aggcgttcag cctctcagct gtttctccct | 120 |
| cgttggcatt tggaagcttg cagtccttca gggaagagac agatttggca ggaacgttct | 180 |
| ttgtgcccgc ctcccttttc tatttttat tttttatttt tttacctgga atagggggca | 240 |
| gatttataat gacagcctta gggaaggggg agaaaaagtt tcagccggca cgacaatgcc | 300 |
| cgttttttcc acagtccaca ctgtgccaca aacagctttg gtgccactcg gagcccgtcc | 360 |
| cccgtcccct ccctctctct ctgcaggctc gcactggcag gcggaggcac agttaaattc | 420 |
| cagcaccttc tccacatacc cccgaactac tacgcgctat tactacggct gccctccgtt | 480 |
| ttcgcttcgc ctcctcccct tccgcagtct ccctggagga gccccgcggc gcccgaggaa | 540 |
| gaggactgcc agggaaggga cagcgggcgc ccagctccag cagggcttgg ggcttttctgc | 600 |
| atcccgcgca gtttctctgc tccaggcaca aacgcggccc gagagccggc gccttgcagt | 660 |
| cacacacgga tccacgcata cagtagagct gtctagatcc acattcttgc acaccgcccc | 720 |
| ctcctccccc cgcgctcccg gagtcgctga gctgagcgag tgacaggcgc gtcccgccaa | 780 |
| cccgcgcccg gacgggcagg gaggagcggc gcgcggggcc aactgcggcg cgtcttccgg | 840 |
| cgccgcgga ggaggcgagg gtgggacgct gggcggagcc cgagtttagg aagaggaggg | 900 |
| gacggctgtc atcaatgaag tcatattcat aatctagtcc tctctccctc tg | 952 |

<210> SEQ ID NO 43
<211> LENGTH: 6
<212> TYPE: DNA
<213> ORGANISM: Artificial Sequence
<220> FEATURE:
<223> OTHER INFORMATION: Synthetic

<400> SEQUENCE: 43

| ttttaa | 6 |

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44

| cttttctatt tttattttt | 20 |

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45 cctttctat tttttatttt t                                         21

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
cttttctatt tttatttt t                                          21

<210> SEQ ID NO 47
<211> LENGTH: 22
<212> TYPE: DNA
<213> ORGANISM: Artificial Sequence
<220> FEATURE:
<223> OTHER INFORMATION: Synthetic

<400> SEQUENCE: 47 cctttctat tttttatttt tt                                        22

<210> SEQ ID NO 48
<211> LENGTH: 18
<212> TYPE: DNA
<213> ORGANISM: Artificial Sequence
<220> FEATURE:
<223> OTHER INFORMATION: Synthetic

<400> SEQUENCE: 48 tatttttat tttttatt                                             18

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49 tatttttat tttttatttt                                           20

<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
gcccgcctcc cttttctatt ttt                                      23

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
cgcctccctt ttctatttt                                           20

```
<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52 ccctttcat tttttatttt ttattt                                       27

<210> SEQ ID NO 53
<211> LENGTH: 7
<212> TYPE: DNA
<213> ORGANISM: Artificial Sequence
<220> FEATURE:
<223> OTHER INFORMATION: Synthetic

<400> SEQUENCE: 53 tattttt                                                            7
```